United States Patent
Yu et al.

(10) Patent No.: US 12,365,919 B2
(45) Date of Patent: *Jul. 22, 2025

(54) SERUM-FREE SUSPENSION SYSTEM FOR LENTIVIRAL PRODUCTION

(71) Applicant: LIFE TECHNOLOGIES CORPORATION, Carlsbad, CA (US)

(72) Inventors: Xin Yu, Suzhou (CN); Xavier de Mollerat du Jeu, Encinitas, CA (US)

(73) Assignee: Life Technologies Corporation, Carlsbad, CA (US)

( * ) Notice: Subject to any disclaimer, the term of this patent is extended or adjusted under 35 U.S.C. 154(b) by 206 days.

This patent is subject to a terminal disclaimer.

(21) Appl. No.: 17/860,833

(22) Filed: Jul. 8, 2022

(65) Prior Publication Data

US 2022/0348964 A1    Nov. 3, 2022

Related U.S. Application Data

(63) Continuation of application No. 15/721,105, filed on Sep. 29, 2017, now Pat. No. 11,414,675.

(60) Provisional application No. 62/402,877, filed on Sep. 30, 2016.

(51) Int. Cl.
*C12N 15/86* (2006.01)
*C12N 7/00* (2006.01)

(52) U.S. Cl.
CPC ............... *C12N 15/86* (2013.01); *C12N 7/00* (2013.01); *C12N 2740/15043* (2013.01); *C12N 2740/15052* (2013.01); *C12N 2740/16043* (2013.01); *C12N 2740/16051* (2013.01)

(58) Field of Classification Search
None
See application file for complete search history.

(56) References Cited

U.S. PATENT DOCUMENTS

| | | |
|---|---|---|
| 2009/0023186 A1 | 1/2009 | Hildinger et al. |
| 2013/0316400 A1 | 11/2013 | Vasu et al. |
| 2015/0211021 A1 | 7/2015 | De Mollerat Du Jeu |
| 2016/0045600 A1 | 2/2016 | De Mollerat Du Jeu et al. |
| 2017/0016043 A1 | 1/2017 | Zmuda et al. |

FOREIGN PATENT DOCUMENTS

| | | |
|---|---|---|
| CN | 104136605 A | 11/2014 |
| CN | 104364369 A | 2/2015 |
| JP | 2014533516 A | 12/2014 |
| JP | 2015515859 A | 6/2015 |
| WO | WO-2013076309 A1 | 5/2013 |

OTHER PUBLICATIONS

Mao et al. "Lentiviral Vectors Mediate Long-Term and High Efficiency Transgene Expression in HEK 293T cells", Int. J. Med. Sci. 2015; 12(5): 407-415 (Year: 2015).*
Tzavelas, et al., Analytical cellular pathology vol. 22 (2001) 223-227 (Year: 2001).*
Backliwal G, et al., "Rational vector design and multi-pathway modulation of HEK 293E cells yield recombinant antibody titers exceeding 1 g/l by transient transfection under serum-free conditions", Nucleic Acids Research, vol. 36, No. 15, Jul. 24, 2008, e96, pp. 1-7.
Backliwal, G. et al., "Valproic Acid: A Viable Alternative to Sodium Butyrate for Enhancing Protein Expression in Mammalian Cell Cultures", Biotechnology and Bioengineering, vol. 101 (1), Sep. 1, 2008, pp. 182-189.
Baldi L, et al., "Large-scale transfection of mammalian cells", Methods in Molecular Biology, vol. 801, Chapter 2, Jan. 1, 2012, pp. 13-26.
Ellis, B. et al., "Creating Higher Titer Lentivirus with Caffeine", Human Gene Therapy, vol. 22, Jan. 2011,93-100.
Leathers R., et al., "ExpiCHO™: Surpassing the Performance of 293 in a Transient CHO Expression System," Poster EP23339, Presented at Drug Discovery 2015, ELRIG, Telford UK (Year: 2015).
PCT/US2017/054511, "International Search Report mailed", Dec. 1, 2017, 5 Pages.
Tzavelas et al., "Effect of Osmolarity and Presence of Serum on the Efficiency of Cell Transfection Using Immunoporation", Analytical Cellular Pathology, vol. 22, 2001, pp. 223-227.
Yang and Xiong "Culture Conditions and Types of Growth Media for Mammalian Cells" Chapter 1 (pp. 3-18 in Biomedical Tissue Culture: ed. Luca Ceccherini-Nelli and Barbara Matteoli. London, UK: IntechOpen Ltd. 2012 (Year: 2012).

* cited by examiner

*Primary Examiner* — Shanon A. Foley
*Assistant Examiner* — Myron G H
(74) *Attorney, Agent, or Firm* — Matthew J. Hierholzer

(57) ABSTRACT

A lentiviral vector production system comprises (a) a lentiviral culture supplement to control cell growth, (b) a transfection reagent comprising DHDMS, DOPE, and cholesterol to increase transfection efficiency, (c) a lentiviral production enhancer comprising sodium propionate, sodium butyrate, and caffeine to boost lentiviral production, wherein the lentiviral vector production system is serum-free. A method of lentiviral vector production comprises using the lentiviral production system. Another method for lentiviral vector production comprises (a) culturing eukaryotic cells in a serum-free medium, (b) providing a lentiviral culture supplement to control cell growth, (c) transfecting the cells with a lentiviral vector using a transfection reagent comprising DHDMS, DOPE, and cholesterol to increase transfection efficiency, and (d) providing a lentiviral production using a lentiviral production enhancer comprising sodium propionate, sodium butyrate capable of boosting lentiviral production.

14 Claims, 9 Drawing Sheets

SERUM-FREE SUSPENSION SYSTEM FOR LENTIVIRAL PRODUCTION

CROSS-REFERENCE TO RELATED APPLICATIONS

This application is a continuation of U.S. patent application Ser. No. 15/721,105 filed Sep. 29, 2017, now pending, which application claims the right of priority under 35 U.S.C. § 119(e) to U.S. Provisional Appl. Ser. No. 62/402,877, filed Sep. 30, 2016 which applications are commonly owned with this application and each of which is hereby expressly incorporated by reference in its entirety as though fully set forth herein.

FIELD

New lentiviral vector production system in large-scale, serum-free suspension.

BACKGROUND

Recently, lentiviral vectors have become the center of attention for use as gene transfer vectors in gene therapy. One current new generation therapy, CAR-T cell therapy, employs lentiviral vectors as efficient gene transfer tool to express engineered Chimeric Antigen Receptors (CAR) on the surface of T-cells to recognize and kill cancer cells. Therefore, preclinical and clinical researchers have demanded lentiviral production on a much larger scale, high-titer, and in animal-serum-free medium. Lentiviral production contributes to the high cost of developing CAR-T cell therapies.

Current lentiviral production systems mainly use adherent cells which need fetal bovine serum to support cell growth in flasks or cell factories. This system is suitable for research purpose at small scale, but not at large scale, which requires large incubators and large cell culture vessels. Culturing adherent cells is harder for the operator and requires more effort to produce large amount of lentiviral vectors, increasing the cost.

Caffeine was previously used to enhance lentiviral vector production in a serum-based culture system, but sodium butyrate, a histone deacetylase inhibitor, was shown to work only ~50% as well as caffeine. Ellis et al., Creating Higher Titer Lentivirus with Caffeine, Human Gene Therapy 22:93-100 (2011).

We have developed a new lentiviral system to produce vectors in a serum free suspension platform and at high titers. This technology employs a newly developed propriety set of good manufacturing process (GMP) reagents comprising of a new media, new cells, new transfection reagent, new lentiviral enhancer, and an optional stabilizer to stabilize unpurified lentiviral vectors in 4° C. conditions for 24-48 hrs. With this new system we are able to deliver ~1.5E+08 (TU/ml) of unconcentrated lentiviral vectors.

SUMMARY

In accordance with the description, a lentiviral vector production system comprises:
a lentiviral culture supplement to control cell growth,
a transfection reagent comprising DHDMS and at least one helper and/or neutral lipid,
a lentiviral production enhancer comprising sodium propionate, sodium butyrate, and caffeine,
wherein the lentiviral vector production system is serum-free.

In some embodiments, wherein the at least one helper and/or neutral lipid comprises DOPE. In some embodiments, the at least one helper and/or neutral lipid comprises DOPE and cholesterol.

In some embodiments, the system is designed for production of lentivirus in suspension 293 cells, 293F cells, or a derivative thereof.

In some embodiments, the 293F cells, or the cells derived therefrom, are capable of growing at a density of from about $1 \times 10^6$ to about $20 \times 10^6$ with less than 20% cell death after 5 days.

In some embodiments, the lentiviral culture supplement comprises: amino acids and/or dipeptides and sugar sources, sugar alcohol, and/or carbon sources. In some embodiments, the lentiviral culture supplement comprises amino acids and glucose.

In some embodiments, the lentiviral culture supplement is added at from about 1% to about 10%. In some embodiments, the osmolality of said glucose in the lentiviral culture supplement is from about 500 mOsm/kg to about 700 mOsm/kg, about 550 mOsm/kg to about 650 mOsm/kg, about 575 mOsm/kg to about 625 mOsm/kg. In some embodiments, concentration of said glucose in the lentiviral culture supplement is from about 85 mg/ml to about 115 mg/ml, about 90 mg/ml to about 110 mg/ml, about 95 mg/ml to about 105 mg/ml.

In some embodiments, the lentiviral culture supplement has an osmolality of from about 1000 mOsm/kg to about 1500 mOsm/kg, about 1100 mOsm/kg to about 1400 mOsm/kg, about 1200 mOsm/kg to about 1300 mOsm/kg, or any osmolality or range therebetween.

In some embodiments, the lentiviral culture supplement has an osmolality of about 1100 mOsm/kg, about 1150 mOsm/kg, about 1200 mOsm/kg, about 1250 mOsm/kg, about 1300 mOsm/kg, about 1350 mOsm/kg, about 1400 mOsm/kg, about 1450 mOsm/kg, about 1500 mOsm/kg.

In some embodiments, DHDMS is included at from about 0.4 to 0.6 mM. In some embodiments, DOPE is included at from about 0.2 to 0.5 mM/mL. In some embodiments, cholesterol is included at from 0.1 to 0.6 mM/mL. In some embodiments, the only helper and/or neutral lipid is DOPE.

In some embodiments, the lentiviral enhancer comprises valproic acid. In some embodiments, sodium propionate and/or sodium butyrate are provided in as an aqueous solution. In some embodiments, caffeine is provided in Lentiviral expression medium. In some embodiments, sodium propionate is included at from about 3 to 15 mM. In some embodiments, sodium butyrate is included at from about 1.5 to 3 mM. In some embodiments, caffeine is included at from about 0.75 to 3 mM. In some embodiments, valproic acid is included at from about 0.5 to 1 mM.

In some embodiments, a method for lentiviral vector production comprises using any of the lentiviral vector production systems described herein.

In some embodiments, a method for lentiviral vector production comprises culturing eukaryotic cells in a serum-free medium, providing a lentiviral culture supplement to control cell growth, transfecting the cells with a lentiviral vector using a transfection reagent comprising DHDMS, DOPE, and cholesterol to increase transfection efficiency, and providing a lentiviral production enhancer comprising sodium propionate, sodium butyrate, and caffeine capable of boosting lentiviral production.

In some embodiments, said cultured eukaryotic cells are in a suspension culture adapted for growth under high density conditions. In some embodiments, the cells are grown in a suspension cell culture having a cell density of at least about $1 \times 10^6$ to $20 \times 10^6$ cells/mL In some embodiments, the method is for the culture of 293 cells, a derivative of 293 cells, 293F cells, or a derivative of 293F cells.

In some embodiments, the method can produce about $2.5 \times 10^8$ TU/ml of unconcentrated lentiviral vectors. In some embodiments, the volume of the suspension cell culture is from about 10 mL to about 5 L. In some embodiments, the cell viability is at least 80% after 5 days.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIG. 1A: At the time of virus production, culture medium was presented with 1%, 5% and 10% of ExpiCHO™-Feed culture supplement with various cell densities. Post-transfection 48 hrs, lentiviral vectors were collected and titers were measured, respectively.

FIG. 1B: Suspension cell viabilities were monitored in the presence of various amount of ExpiCHO™-Feed supplement.

FIG. 2A: JMP® Design of Experiments (DoE) designed new transfection reagents were screened in this experiment. A total of 12 candidates were designed and 8 of the 12 new transfection reagents were chosen for next DoE run.

FIG. 2B: Several more JMP® designed DoE experiments were conducted (data not shown). 12 reagents were chosen based on performance and formulation compositions.

FIG. 3A: 32 candidates including a control lentiviral enhancer were tested.

FIG. 3B and FIG. 3C show analysis by JMP® and the prediction profiler graph from two DoE enhancer experiments.

DESCRIPTION OF THE EMBODIMENTS

Figure 1A:
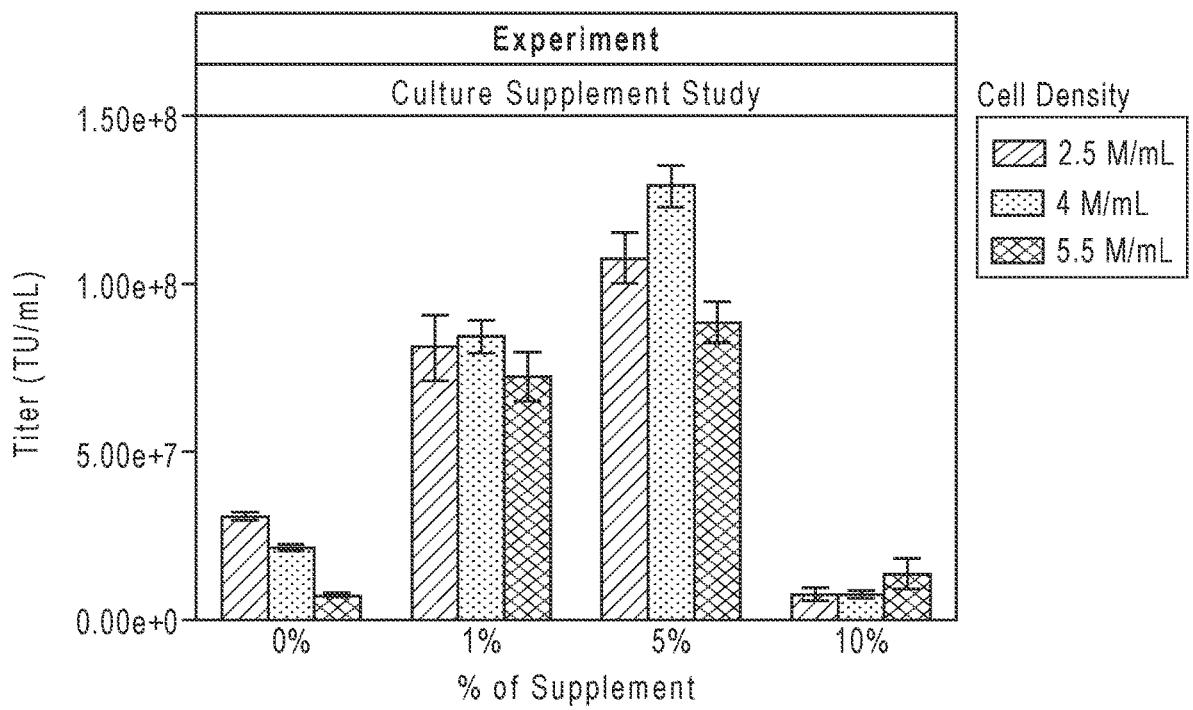
FIGS. 1A and 1B show the impact of culture supplement in lentiviral production.

I. A Lentiviral Production System
A. Cells

The term "cell" as used herein refers includes all types of eukaryotic and prokaryotic cells. In some embodiments, the term refers to eukaryotic cells, especially mammalian cells. In certain exemplary though non-limiting embodiments, the term "cell" is meant to refer to human embryonic kidney (HEK) or human 293 cells, or a variant thereof, such as, e.g., a 293 variant that can grow in suspension. In some embodiments, variants of 293 cells that can grow, proliferate and be transfected in suspension culture, in particular those variants that can be cultured at high density (e.g., ≥about $2 \times 10^6$ cells/ml, greater ≥about $3 \times 10^6$ cells/ml, or even optionally ≥about $4 \times 10^6$ cells/ml or about $20 \times 10^6$ cells/ml). An example of such a variant are 293F cells, such as EXPI293™ F cells.

In some embodiments, the term "high density" when used in the context of culturing cells and conducting transfection workflows, generally refers to a known cell line, or a variant of a known cell line, that can be grown or cultured in an appropriate cell culture medium to densities of ≥about $1 \times 10^6$ cells/ml, ≥about $2 \times 10^6$ cells/ml, ≥about $3 \times 10^6$ cells/ml, or even optionally ≥about $4 \times 10^6$ cells/ml, or ≥about $20 \times 10^6$ cells/ml, while still retaining the ability to be transfected at high efficiency and are able to express a target protein at high levels (e.g., levels at or exceeding 200 µg/ml to up to about 1 mg/ml or more).

In some embodiments, the cells are adapted for high density cell culture. This refers to a cell lineage or a (non-clonal) population of cells derived from the same parental cell lineage that has been adapted to grow at high density in a high-density culture medium while retaining cell viability at or above about 80%. Such cells may be isolated or selected out from the parental population of cells by maintaining the cells at high density ≥about 40, 50, 60, 70, or 80 sequential passages and gradually replacing the proportion of growth medium with the desired high-density culture medium. Optionally, during the process, different pools of cells may be individually propagated and subjected to the selection procedure while simultaneously assessing transfection efficiency and or lentivirus vector production efficiency, so that non-clonal population of cells may be selected that can be sustained and grown at high density, transfected with high efficiency, and express high levels of a desired recombinant protein. While it will be readily apparent to the skilled practitioner that a variety of cell types and lineages may be subjected to this selection procedure, it has been determined that cell lineages derived from 293 fibroblast cells are particularly amenable to the selection process for being adapted to high density growth conditions. In some scenarios, cells that are adapted to high density growth culture and amenable for use herein will also be capable of being transfected at high efficiency and/or capable of expressing recombinant protein at yield exceeding at least about 200 µg/mL of cell culture up to about 2 mg/mL of cell culture, more typically between about 500 µg/ml of cell culture to about 1 mg/mL of cell culture. In some scenarios, cells adapted for high density culture used are capable of being sustained and transfected at densities in the range from about $1 \times 10^6$ to about $20 \times 10^6$ cells/ml, about $2 \times 10^6$ to about $2 \times 10^6$ cells/ml, or about $2.5 \times 10^6$ to about $6 \times 10^6$ cells/ml. In some embodiments, cells may be adapted for high density culture and transfected at densities in the range from about 1×10⁶ to about 20×10⁶, from about 1×10⁶ to about 4×10⁶, from about 1×10⁶ to about 3×10⁶, from about 1×10⁶ to about 2×10⁶.

In some embodiments, the cells are grown in a suspension culture. This includes a cell culture in which the majority or all of the cells in a culture vessel are present in suspension, and the minority or none of the cells in the culture vessel are attached to the vessel surface or to another surface within the vessel. In some embodiments, suspension culture has ≥about 75% of the cells in the culture vessel are in suspension, not attached to a surface on or in the culture vessel. In some embodiments, a suspension culture has ≥about 85% of the cells in the culture vessel are present in suspension, not attached to a surface on or in the culture vessel. In some embodiments, suspension culture has ≥about 95% of the cells in the culture vessel present in suspension, not attached to a surface on or in the culture vessel.

The lentiviral vector production system allows wherein the 293F cells, or the cells derived therefrom, to be capable of growing at a density of from about 1×10⁶ to about 20×10⁶ with less than 20% cell death after 5 days.

B. Lentiviral Culture Supplement

The lentiviral production system includes a lentiviral culture supplement. The lentiviral culture supplement serves to control cell growth, slowing down the cell growth during production time and allowing the maximum production of lentiviral vector production and minimizes virus "devoured" by untransfected cells. See FIGS. 1A and 1B.

In certain embodiments, the lentiviral culture supplement comprises a cell culture feed, optionally comprising glucose and amino acids. One exemplary cell culture supplement, or feed, is CTS™ LV-MAX™, while another exemplary cell culture supplement, or feed, is ExpiCHO™ Feed (a Thermo Fisher Scientific product in the ExpiCHO™ Expression System).

In some embodiments, the lentiviral culture supplement comprises amino acids, dipeptides, sugar sources, sugar alcohol, and carbon sources. In some embodiments, the lentiviral culture supplement further comprises minerals and/or trace metals and/or vitamins and/or vitamin precursors.

In some embodiments, dipeptides include L-alanyl-L-cysteine and L-alanyl-L-tyrosine. In some embodiments, amino acids include any amino acid or any essential amino acid. In some embodiments, term "amino acid" refers to amino acids or their derivatives (e.g., amino acid analogs), as well as their D- and L-forms. Examples of such amino acids include glycine, L-alanine, L-asparagine, L-cysteine, L-aspartic acid, L-glutamic acid, L-phenylalanine, L-histidine, L-isoleucine, L-lysine, L-leucine, L-glutamine, L-arginine, L-methionine, L-proline, L-hydroxyproline, L-serine, L-threonine, L-tryptophan, L-tyrosine, and L-valine, N-acetyl cysteine. In some embodiments, amino acids included in the culture supplement include glycine, alanine, arginine, asparagine, aspartic acid, glutamic acid, histidine, hydroxyproline, isoleucine, leucine, lysine, methionine, phenylalanine, proline, serine, threonine, tryptophan, and/or valine. In some embodiments, sugar sources, sugar alcohol, and carbon sources include D-glucose, i-Inositol, and sodium pyruvate. In some embodiments the supplement comprises glucose.

In some embodiments, the lentiviral culture supplement comprises the components listed in Table 1.

TABLE 1

Lentiviral Culture Supplement

| Catalog # | Component | Range (g/L) |
|---|---|---|
| 100009922 | AOF – L-Alanyl-L-Cysteine Dimer | .1 to 10 |
| 100009921 | AOF – L-Alanyl-L-Tyrosine Dihydrate | .1 to 10 |
| 8205023 | D-Glucose | 50 to 200 |
| 8101006 | Glycine | .01 to 1 |
| 8101002 | L-Alanine | .1 to 1 |
| 8101009 | L-Arginine HCl | 1 to 10 |
| 8101014 | L-Asparagine H₂O | 1 to 10 |
| 8101016 | L-Aspartic Acid | .1 to 10 |
| 8101048 | L-Glutamic Acid | .1 to 10 |
| 8101062 | L-Histidine HCl H₂O | .1 to 10 |
| 8101097 | L-Hydroxyproline | .1 to 10 |
| 8101072 | L-Isoleucine | .1 to 10 |
| 8101077 | L-Leucine | .1 to 10 |
| 8101083 | L-Lysine HCL | .1 to 10 |
| 8101086 | L-Methionine | .1 to 10 |
| 8101095 | L-Phenylalanine | .1 to 10 |
| 8101096 | L-Proline | .1 to 10 |
| 8101101 | L-Serine | .1 to 10 |
| 8101104 | L-Threonine | .1 to 10 |
| 8101110 | L-Tryptophan | .1 to 10 |
| 8101116 | L-Valine | .1 to 10 |

In some embodiments, the lentiviral culture supplement is added at from about 1% to about 10%. In some embodiments, the lentiviral culture supplement is added at about 1%, 3.5%, 5%, or 10%. In some embodiments, the lentiviral culture supplement is added at about 3.5%.

In some embodiments, the lentiviral culture supplement may include glucose. In some embodiments, the osmolality of glucose in said lentiviral culture supplement may be from about 500 mOsm/kg to about 700 mOsm/kg, about 550 mOsm/kg to about 650 mOsm/kg, about 575 mOsm/kg to about 625 mOsm/kg. In some embodiments, concentration of glucose in the lentiviral culture supplement may be from about 85 mg/ml to about 115 mg/ml, about 90 mg/ml to about 110 mg/ml, about 95 mg/ml to about 105 mg/ml.

In some embodiments, the lentiviral culture supplement may include a plurality of amino acids, each amino acids having a concentration from about 0.1 mg/ml to about 8 mg/ml. In some embodiments, the lentiviral culture supplement may have an osmolality of from about 1000 mOsm/kg to about 1500 mOsm/kg, about 1100 mOsm/kg to about 1400 mOsm/kg, about 1200 mOsm/kg to about 1300 mOsm/kg, or any osmolality or range therebetween. In some embodiments, the lentiviral culture supplement may have an osmolality of about 1100 mOsm/kg, about 1150 mOsm/kg, about 1200 mOsm/kg, about 1250 mOsm/kg, about 1300 mOsm/kg, about 1350 mOsm/kg, about 1400 mOsm/kg, about 1450 mOsm/kg, about 1500 mOsm/kg.

In some embodiments, the lentiviral culture supplement has an osmolality of from about 1000 mOsm/kg to about 1500 mOsm/kg, about 1100 mOsm/kg to about 1400 mOsm/kg, about 1200 mOsm/kg to about 1300 mOsm/kg, or any osmolality or range therebetween. In some embodiments, the lentiviral culture supplement has an osmolality of about 1100 mOsm/kg, about 1150 mOsm/kg, about 1200 mOsm/kg, about 1250 mOsm/kg, about 1300 mOsm/kg, about 1350 mOsm/kg, about 1400 mOsm/kg, about 1450 mOsm/kg, about 1500 mOsm/kg.

C. Transfection Reagent

The lentiviral production system also comprises transfection reagent or a composition that facilitates entry of a macromolecule into a cell. In one embodiment, the transfection reagent comprises a cationic lipid and one or more neutral/helper lipids as a "lipid aggregate."

In some embodiments, lipid aggregates can include at least a first cationic lipid and optionally at least a first neutral lipid, wherein said lipid aggregate is suitable for forming a cationic complex with a nucleic acid under aqueous conditions, wherein said the cationic lipids have the structure:

(Formula (I))

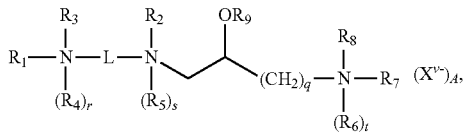

and salts thereof; where:

$R_1$ and $R_2$, independently, are an alkyl, alkenyl or alkynyl groups, having from 8 to 30 carbon atoms;

an alkyl, alkenyl or alkynyl groups, having from 8 to 30 carbon atoms and optionally substituted by one or more of an alcohol, an aminoalcohol, an amine, an amide, an ether, a polyether, an ester, a mercaptan, alkylthio, or a carbamoyl group or where R1 is —$(CH_2)_q$—$N(R_6)_rR_7R_8$;

$R_3$ and $R_4$, independently, are hydrogens, or alkyl, alkenyl or alkynyl groups having from 8 to 30 carbon atoms and optionally substituted by one or more of an alcohol, an aminoalcohol, an amine, an amide, an ether, a polyether, an ester, a mercaptan, alkylthio, or a carbamoyl group;

$R_5$-$R_8$, independently, are hydrogens, or alkyl, alkenyl or alkynyl groups;

$R_9$ is a hydrogen, or an alkyl, alkenyl or alkynyl group, a carbohydrate or a peptide;

r, s and t are 1 or 0 to indicate the presence or absence of the indicated R group, when any of r, s or t are 1 the nitrogen to which the indicated R group is attached is positively charged and wherein at least one of r, s or t is 1;

q is an integer ranging from 1 to 6, inclusive;

$X^{v-}$ is an anion, where v is the valency of the anion and A is the number of anions;

L is $(CH_2)_n$, where n is an integer ranging from 1 to 10, inclusive, which is optionally substituted with one or more $ZR_{10}$ groups, where Z is O or S, and $R_{10}$ is hydrogen or an alkyl, alkenyl or alkynyl group; or {—$(CH_2)_k$—Y—$(CH_2)_m$}$_p$—, where k and m, independently, are integers ranging from 1 to 10, inclusive, and p is an integer ranging from 1 to 6, inclusive, and Y is O, S, CO, COO, $CONR_{11}$, $NR_{11}CO$, or $NR_{11}COR_{11}N$ where $R_{11}$, independent of any other $R_{11}$, is hydrogen or an alkyl group;

wherein one or more $CH_2$ groups of the alkyl, alkenyl or alkynyl groups of $R_1$-$R_{10}$ can be replaced with an O, S, S—S, CO, COO, $NR_{12}CO$, $NR_{12}COO$, or $NR_{12}CONR_{12}$ where $R_{12}$, independent of any other $R_{12}$, is hydrogen or an alkyl, alkenyl or alkynyl group; and wherein the alkyl, alkenyl or alkynyl groups of $R_1$-$R_{12}$ are optionally substituted with one or more $OR_{13}$, CN, halogens, $N(R_{13})_2$, peptide, or carbohydrate groups where $R_{13}$, independently of other $R_{13}$, is hydrogen or an alkyl, alkenyl or alkynyl group, and wherein at least one of $R_3$ and $R_4$, when present as alkyl groups, are substituted with both $OR_{13}$ and $N(R_{13})_2$ groups.

In one embodiment the cationic lipid is DHDMS (dihydroxyl-dimyristylspermine tetrahydrochloride salt) according to the following structure:

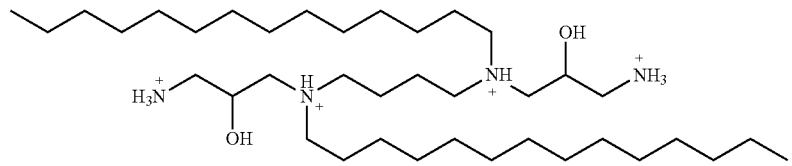

In some embodiments, the neutral (or helper) lipids may be selected from the following; DOPE, cholesterol, or DOPC. In one embodiment, a neutral lipid may be one of cholesterol, DOPE, or DOPC. In an embodiment, the neutral lipid is cholesterol. In an embodiment, a neutral lipid is DOPE. In an embodiment, the neutral lipid is DOPC. In some embodiments, two neutral lipids are employed, for example, DOPE and cholesterol. In some embodiments, only one neutral lipid is employed.

In some embodiments, the transfection reagent comprises DHDMS, DOPE, and cholesterol. In some embodiments, the mole ratio of the transfection reagents DHDMS:DOPE:cholesterol ranges from about 0.4 to 0.65 mM DHDMS, from about 0.1 or 0.125 to 0.25 DOPE, and from about 0.2 to 0.4 or 0.375 cholesterol. In some embodiments, the mole ratio of the transfection reagents DHDMS:DOPE:cholesterol ranges from about 0.45 to 0.55 mM DHDMS, from about 0.1 to 0.25 DOPE, and from about 0.3 to 0.4 cholesterol. In some embodiments, the mole ratio of the transfection reagents DHDMS:DOPE:cholesterol ranges from about 0.475 to 0.5 mM DHDMS, from about 0.1 to 0.125 DOPE, and from about 0.325 to 0.35 cholesterol. In some embodiments, the mole ratio of the transfection reagents DHDMS:DOPE:cholesterol ranges from about 0.5 to 0.525 mM DHDMS, from about 0.125 to 0.15 DOPE, and from about 0.35 to 0.375 cholesterol. The transfection reagent is suitable for delivery of multiple plasmids at high cell density. See FIGS. 2A-D.

In some embodiments, the DHDMS is included at from about 0.4 to 0.65 mM. In some embodiments, the DOPE is included at from about 0.05 to 0.5 mM/mL. In some embodiments, the cholesterol is included at from 0.1 to 0.6 mM/mL.

In some embodiments, DHDMS and DOPE are included. In some embodiments, the ratio of DHDMS:DOPE ranges from about 0.6:0.4 to 0.7:0.3. In some embodiments, the ratio of DHDMS:DOPE ranges from about 0.625:0.375 to 0.675 to 0.325. In some embodiments, the ratio of DHDMS:DOPE ranges from about 0.6 to 0.4 to 0.625 to 0.375.

In some embodiments, the ratio of DHDMS:DOPE:cholesterol (including any zero amounts) may be chosen from those in Table 2, with all numbers considered to be modified by "about." Other helper and/or neutral lipids can be substituted for the DOPE and/or cholesterol.

TABLE 2

Some Embodiments of DHDMS, DOPE, and cholesterol:

| DHDMS | DOPE | cholesterol |
|---|---|---|
| 0.4000 | 0.2575 | 0.3425 |
| 0.4000 | 0.2616 | 0.3384 |
| 0.4965 | 0.2386 | 0.2649 |
| 0.5200 | 0 | 0.4800 |
| 0.6000 | 0 | 0.4000 |
| 0.6000 | 0.2000 | 0.2000 |
| 0.6000 | 0.4000 | 0 |
| 0.650 | 0.350 | 0 |
| 0.473 | 0.228 | 0.299 |
| 0.512 | 0.208 | 0.279 |
| 0.519 | 0.126 | 0.355 |

In some embodiments, the mole ratio of DHDMS:DOPE:cholesterol (including any zero amounts) is selected from Table 2, Table 5 or Table 6, with all numbers considered to be modified by "about."

In some embodiments, the mole ratio of DHDMS:DOPE:cholesterol is selected from run number 1×R3, 1×R4, 1×R6, 1×R7, 1×R9, 1×R10, 1×R11, 1×R12 from Table 5 or 2b×R13 or 2b×R14 from Table 6.

In some aspects and optionally applied to any of the ratios discussed in the preceding paragraphs in this section, the mole ratio of DHDMS:DOPE:cholesterol adds to 1.0 and the DHDMS mole ratio ranges from about 0.4 to 0.6, the DOPE mole ratio ranges from about 0.2 to 0.5, and the cholesterol mole ratio ranges from about 0.1 to 0.6. For instance, if DHDMS is at a mole ratio of 0.5 and DOPE is at a mole ratio of 0.2, then the cholesterol mole ratio is 0.3 so that the mole ratio adds to 1.0.

D. Lentiviral Production Enhancer

The lentiviral production system also comprises a lentiviral production enhancer. The lentiviral production enhancer comprises sodium propionate, sodium butyrate, and caffeine.

In some embodiments, the sodium propionate and/or sodium butyrate are provided in water. In some embodiments, the caffeine is provided in cell culture expression medium, such as Expi293™ expression medium. In some embodiments, caffeine may be dissolved in media to a final concentration of 40 mM.

In some embodiments, sodium propionate is included at from about 7.5 to 15 mM. In some embodiments, sodium butyrate is included at from about 1.5 to 3 mM. In some embodiments, caffeine is included at from about 0.75 to 3 mM.

In some embodiments, sodium propionate is included at from about 3 to about 5 mM. In some embodiments, sodium propionate is included at from about 5 to 8 mM. In some embodiments, sodium butyrate is included at from about 1.5 to 2.5 mM. In some embodiments, sodium butyrate is included at from about 2.5 to 3 mM. In some embodiments, caffeine is included at from about 2 to 3 mM. In some embodiments, caffeine is included at from about 1 to 2 mM.

In some embodiments, the amounts of valproic acid, sodium propionate, sodium butyrate, and caffeine, respectively, may be chosen from those provided in Table 3, with all numbers considered to be modified by "about."

TABLE 3

Some Embodiments of Lentiviral Production Enhancer Ingredients

| Valproic Acid (mM) | Sodium Propionate (mM) | Sodium Butyrate (mM) | Caffeine (mM) |
|---|---|---|---|
| 0 | 7.5 | 3 | 0.75 |
| 0 | 7.5 | 3 | 1.5 |
| 0 | 15 | 3 | 1.5 |
| 0.5 | 7.5 | 1.5 | 0 |
| 0.5 | 11.25 | 1.5 | 0.75 |
| 0.5 | 11.25 | 1.5 | 0.75 |
| 0.5 | 11.25 | 3 | 1.5 |
| 0.5 | 15 | 0 | 1.5 |
| 0 | 4.53 | 2 | 1.5 |
| 0.5 | 15 | 3 | 0.75 |
| 1 | 7.5 | 3 | 0 |
| 1 | 11.25 | 3 | 0 |
| 1 | 15 | 0 | 0 |
| 1 | 15 | 1.515 | 1.5 |
| 1 | 15 | 3 | 0 |
| 1 | 15 | 3 | 1.5 |

In some embodiments, the lentiviral production enhancer ingredients are chosen from any of those in Table 3, Table 7, or Table 8, with all numbers considered to be modified by "about." In some embodiments, the enhancer ingredients are chosen from any of those in runs 1×R5, 1×R6, 1×R13, 1×R14, 1×R15, 1×R16, 1×R17, 1×R18, 1×R19, 1×R22, 1×R26, 1×R27, 1×R29, 1×R30, or 1×R31 in Table 7.

In some embodiments, the lentiviral production enhancer optionally comprises valproic acid. In some embodiments, the lentiviral production enhancer does not comprise valproic acid. In some embodiments, valproic acid may be included at from about 0.5 to 1 mM.

In some embodiments, the lentiviral production enhancer is added at one or more than one time point, such as at the time of transfection (about hour 0) until about 48 hours after transfection. The lentiviral production enhancer may be added at about 16 hours after transfection to boost cell packaging of lentiviral vectors. In some embodiments, the lentiviral production enhancer may be added at the time of transfection. In some embodiments, the lentiviral production enhancer may be added at the time of transfection and at about 16 hours after transfection. In some embodiments, lentiviral production enhancer may be added from about 10 to 16 hours after transfection.

E. Cell Culture Medium

A variety of cell culture medium may be used to culture the lentiviral production system cells. Serum free media are often desired by investigators. Any serum-free medium that supports the growth of the cells described above in section I.A above may be used. The medium may also be protein free.

A "serum-free medium" (sometimes referred to as "SFM Medium") is a medium that contains no serum (e.g., fetal bovine serum (FBS), calf serum, horse serum, goat serum, human serum, etc.) and is generally designated by the letters SFM. The phrase "protein-free" culture media refers to culture media that contain no protein (e.g., no serum proteins such as serum albumin or attachment factors, nutritive proteins such as growth factors, or metal ion carrier proteins such as transferrin, ceruloplasmin, etc.). In some embodiments, if peptides are present, the peptides are smaller peptides, e.g., di- or tri-peptides. In some embodiments, peptides of deca-peptide length or greater are no more than about 1%, no more than about 0.1%, and no more than about 0.01% of the amino acids present in the protein free medium.

In some embodiments, the cell culture medium is Expi293™ expression medium (Thermo Fisher Scientific Cat #A14351-01). This medium is a chemically-defined, specialty medium specifically developed for the high-density suspension culture and transfection of 293 cells and contains no human or animal-origin products. Expi293™ expression medium is formulated with GlutaMAX™-I reagent. For suspension growth and transfection applications, this medium may be used without any supplementation. Additionally, antibiotics are not necessary; however, 5 mL/L of antibiotic-antimycotic (Thermo Fisher Scientific Cat #15240) containing penicillin, streptomycin, and amphotericin B may be used when beneficial.

In some embodiments, a high-density culture media may be used, including any culture medium capable of sustaining the growth of mammalian cells, in some embodiments, cells growing in suspension, at densities of up to about $2\times10^7$ cells/ml while maintaining viability of said cells in excess of about 80% and further, maintaining the ability of said suspension cells to be efficiently transfected and express high amounts of recombinant protein. The high density culture medium used may vary between different applications and uses, and may depend on the nature of the cell line being used, the desired protein being transiently expressed, the nature of the transfection modality selected for transfer of the expression vector into cells, and the amount and nature of any expression enhancers added to the system as described below. Nevertheless, high density culture medium contemplated for use in the present transient expression systems and methods will typically be serum-free, protein-free, allow the cultivation and growth of suspension cells to a density of up to about $2\times10^7$ cells/ml, more typically between about $2\times10^6$ cells/ml to about $1\times10^7$ cells/ml, and will further enable the yield of protein produced in the transient expression system to exceed at least 200 μg/mL of cell culture up to 2 mg/mL of cell culture, more typically between about 500 μg/ml of cell culture to about 1 mg/mL of cell culture. In some embodiments, the high density culture medium used will facilitate the transfection of cells at densities in the range of about $1\times10^6$ to about $20\times10^6$ cells/ml, about $2\times10^6$ to about $2\times10^6$ cells/ml, or about $2.5\times10^6$ to about $6\times10^6$ cells/ml.

Exemplary high density culture media suitable for use herein include, though are not limited to, HuMEC Basal Serum free Medium, KNOCKOUT™ CTS™ XenoFREE ESC/iPSC Medium, STEMPRO™-34 SFM Medium, STEMPRO™ NSC Medium, ESSENTIAL™-8 Medium, Medium 254, Medium, 106, Medium, 131, Medium, 154, Medium, 171, Medium 171, Medium 200, Medium 231, HeptoZYME-SFM, Human Endothelial-SFM, GIBCO® FREESTYLE™ 293 Expression Medium, Medium 154CF/PRF, Medium 154C, Medium 154 CF, Medium 106, Medium 200PRF, Medium 131, Essential™-6 Medium, STEMPRO™-34 Medium, Gibco® Astrocyte Medium, AIM V® Medium CTS™, AMINOMAX™ C-100 Basal Medium, AMINOMAX™-II Complete Medium, CD FORTICHO™ Medium, CD CHO AGT Medium, CHO-S-SFM Medium, GIBCO® FREESTYLE™ CHO Expression Medium, CD OPTICHO™ Medium, CD CHO Medium, CD DG44 Medium, SF-900™ Medium, EXPI293™ Expression Medium, LHC Basal Medium, LHC-8 Medium, 293 SFM Medium, CD 293 Medium, AEM Growth Medium, PER. C6® Cell Medium, AIM V® Medium, EXPILIFE® Medium, Keratinocyte-SFM Medium, LHC Medium, LHC-8 Medium, LHC-9 Medium, and any derivatives or modifications thereof. In certain nonlimiting embodiments, a high density culture media may be CD FORTICHO™ Medium, CD CHO AGT Medium, CHO-S-SFM Medium, GIBCO® FREESTYLE™ CHO Expression Medium, CD OPTICHO™ Medium, CD CHO Medium, CD DG44 Medium, GIBCO® FREESTYLE™ 293 Expression Medium, EXPI293™ Expression Medium, or a like medium, or a modified version thereof. The above listed exemplary high density culture media may be particularly suitable for the high density growth, propagation, transfection and maintenance of 293 cells, a 293 cell variant, or any other cells adapted for use in a high density culture system.

F. Lentiviral Plasmids

A variety of lentiviral plasmids may be used in the present methods. For example, one or more of the lenti expression (transfer) plasmid, pLenti6.3/V5-GW/EmGFP, and lenti packaging plasmid, ViraPower™ Lentiviral Packaging Mix, may be used. Other lentiviral vectors, including #277.pCCLsin.cPT.hPGK.eGFP,Wpre (277-eGFP) may be used. Other nonlimiting lentiviral plasmids may also be used.

Both integration competent and integration deficient lentiviral vectors may be used (ICLV and IDLV, respectively).

Figure 5:
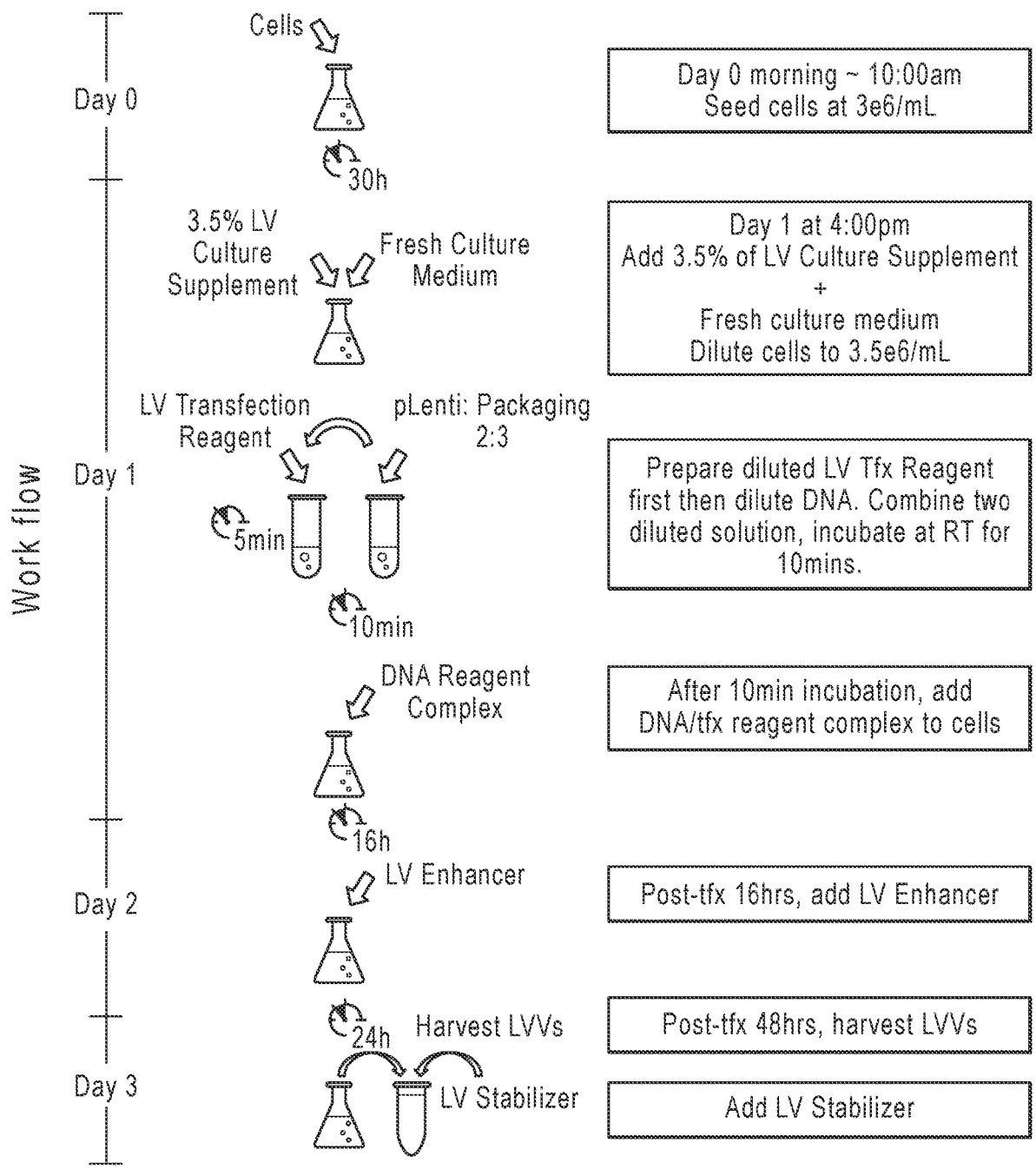
FIG. 5 provides one embodiment of a serum-free large-scale suspension lentiviral production protocol.

A serum-free large scale suspension lentiviral production protocol is shown in FIG. 5. This is one embodiment of a method of using the lentiviral production system described herein.

The present serum-free suspension LV production system is easy to use, scalable, and highly efficient. The system can produce ten times more lentiviral vectors than prior methods. The present system and transfection reagent can efficiently deliver lentiviral expression and package vectors into serum-free suspension growing cells at high cell density. And the culture supplement maintains cells in the middle log phase in order to yield a maximum amount of lentiviral particles. Thus the advantages of this system and its components include simplicity, homogeneity of culture, high lentiviral titer production, ease of scale-up, and feasibility for sealed automation of a lentiviral production system.

II. Methods for Use in a Lentiviral Production System

A. A First Lentiviral Production System

The following guidelines for culture of lentiviral suspension cells may be followed. The cells may be grown according to standard lentiviral suspension cell culture protocols. The cells may be subcultured when they reach a density of approximately $4\times10^6$ to $5\times10^6$ viable cells/mL, typically every 3-4 days. The cells may be split to $0.3\times10^6$ to $0.6\times10^6$ cells, after about 3 or 4 days of culture. The cell growth may be monitored by counting the cells daily at the same time every day. Cell doubling time is about 24 hours. After two weeks from the thawing date, cells are ready for lentiviral production. During cell culture, an orbital shaker may be used at about 125 rpm for 125 mL to 1 L shaker flasks. The incubator may be set to about 37° C., about 8% $CO_2$, and about 75-80% humidity. The culture medium may be warmed in an about 37° C. water bath before use.

Reagents and Methods:
- 125 mL polycarbonate, disposable, sterile, Vent-up Erlenmeyer shaker flask;
- 15 mL sterile conical tube;
- 50 mL sterile conical tube;
- Opti-MEM® I medium;
- Lenti expression (transfer) vector: pLENTI6.3/V5-GW-EmGFP;
- Lenti packaging mix: ViraPower Lentiviral Packaging Mix;
- Lentiviral suspension cells;
- Lentiviral culture supplement;
- Lentiviral transfection reagent;

Lenitviral enhancer

If cells are split on Friday morning to a cell count of $0.6\times10^6$ cells/mL, for example, they may be cultured for 3 days in 1 L flask at about 250 mL culture medium. On Monday morning at 10:00 am, for example, the cells are prepared by counting the cells, and a cell density of around $4.5\times10^6$ cells/mL may be expected. The cells may be diluted in fresh warmed culture medium to $3.0\times10^6$ cells/mL and cultured for another 30 hours.

The transfection may be carried out on Tuesday afternoon at 4:00 pm, for example. The cells may be counted with about 5.5 to $6.0\times10^6$ cells/mL expected. Table 4 provides additional transfection guidelines.

TABLE 4

Transfection of Cells

| | 1 mL | 30 mL |
|---|---|---|
| Cell Density (1 × 10⁶ cells/mL) | $3.5 \times 10^6$ cells/mL | $105 \times 10^6$ cells/mL |
| % LV Culture Supplement | 3.5% (350 µl) | 3.5% (1.05 mL) |
| Total DNA (µg) ViraPower ™: pLenti = 3:2 (µg:µg) | 2.5 µg (1.5 µg + 1 µg) | 75 µg (45 µg + 30 µg) |
| LV Transfection Reagent | 5 µL | 150 µL |
| Opti-MEM ® I (for complexation) | 2 × 75 µL | 2 × 2.25 mL |
| LV Enhancer | 40 µL | 1.2 mL |
| LV Stabilizer | 10 µL | 300 µL |

On Tuesday afternoon, the cells may be seeded with lentiviral supplement. If a 30 mL transfection is selected it may be conducted with high density cells, such as $105\times10^6$ cells/mL in 17.5 mL. 3.5% lentiviral culture supplement may be added, which would be 1.5 mL in a 30 mL transfection. Fresh warmed culture medium may be used to a total volume of 25.5 mL (6.95 mL of fresh media because 1.05 mL of lentiviral culture supplement and 17.5 mL of cell suspension were used). The other 4.5 mL to achieve a total volume of 30 mL may be added from the DNA/reagent complex.

The DNA/transfection reagent may be prepared as follows. Two tubes may be labeled Tube-1 and Tube-2. In Tube-1: 2.25 of Opti-MEM® I medium and 150 µL of lentiviral transfection reagent may be mixed and incubated for about 5 minutes at room temperature. In Tube-2:2.25 mL of Opti-MEM® I medium may be mixed with 45 µg (µL) ViraPower™ Lentiviral Packaging Mix (ViraPower 1 µg/µL) and 30 µg (µL) pLenti6.3/V5-GW/EmGFP plasmid (pLenti expression vector 1 µg/µL). Tube-1 and Tube-2 may be combined by adding Tube-2 solution to Tube-1 with mixing.

The complex solution may be incubated at room temperature for 10 minutes. After 10 minutes of incubation, 4.5 mL of DNA/reagent complex may be added to the prepared cells.

The next day (Wednesday morning, at 9:00 am), add 1.2 mL of LV Enhancer to the flask.

At 48 hours post transfection (Thursday afternoon, at 4:00 pm), harvest LVVs in a 50 mL sterile conical tube and spin down the cells at 3000 rpm, at room temperature for 10 minutes. Collect the supernatant and spin again at 3000 rmp for 10 minutes. Collect the supernatant and run through a 0.45 µM filter.

Optionally add lentiviral stabilizer to the collected supernatant in order to adjust the pH after the virus has been harvested. Lentiviral stabilizer may optionally be added as 1% of the collected supernatant (~300 µL). In some situations, the production system pH is adjusted from about 5 to 8 to stabilize the virus.

Store the lentiviral vectors in 4 C for the next day purification and measure the virus titer by infecting Ht1080 cells at serial dilutions of lentiviral vectors, as described as follows.

Measurement of lentiviral titer (GFP+) may be conducted as follows.

Materials:
Lentivirus: collect cell supernatant or concentrated lentiviral vectors;
Cell line: HT1080;
Culture Medium: Gibco® DMEM high glucose, GlutaMAX™ Supplement, pyruvate+10% FBS;
Polybrene® (stock solution): 100 mg/mL in sterile $H_2O$ (Fisher Scientific NCO663391); and
Costar 96-well round bottom plate for dilutions (Fisher Scientific 05539200).

On Day 1 (morning), begin the measurement of lentiviral titer using a 96-well plate format for high throughput flow analysis. In the morning at 11:00 am, seed a 96-well plate with HT1080 cells at a density of 7000 cells/well in 100 µL of culture media (~30% confluent at time of infection).

Figure 6:
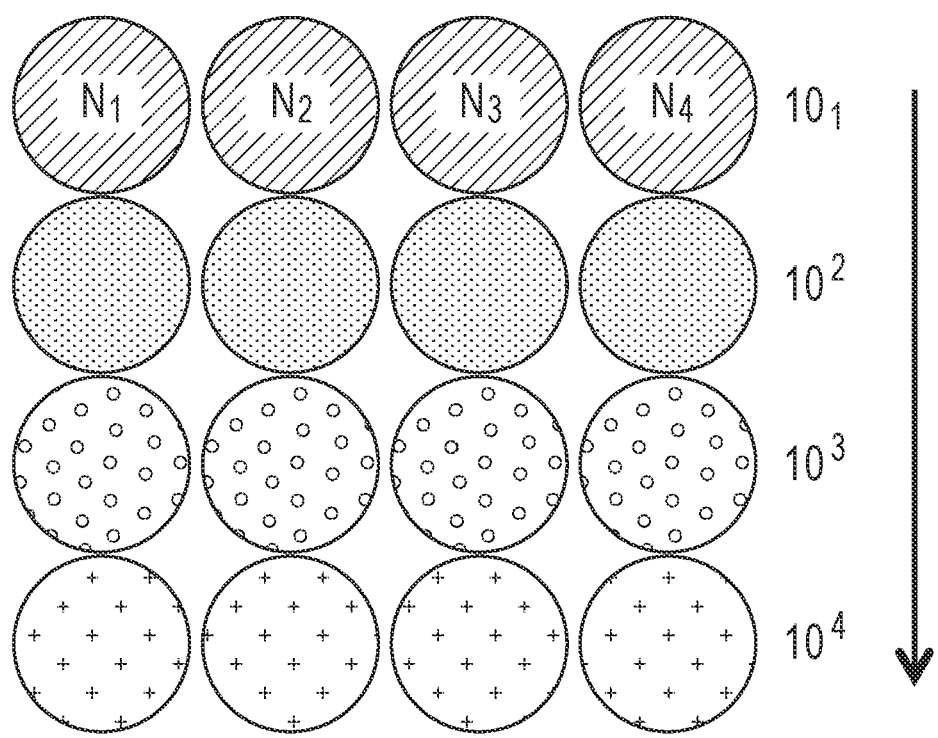
FIG. 6 provides a 4-well-by-4-well pattern for use in the measurement of lentiviral titer Example 6.

In the afternoon at 4:00 pm, prepare fresh virus dilutions as follows. (A) Combine 15 mL of fresh culture medium and 12 µL of 10 mg/mL Polybrene® (final concentration of 8 µg/mL). Vortex well to combine. (B) Per-viral sample, add 135 µL of medium prepared in (A) to 16 wells of a 96-well round bottom plate in a 4-well-by-4-well pattern (see FIG. 6). (C) Add 15 µL of one sample of lentiviral supernatant (or concentrated viral aliquot) to each well in row 1 (total volume 150 µL in each well). (D) Mix well using a pipette (1:10). (E) Perform serial dilution of Row 1 (using a multichannel pipette if available) by transferring 15 µL from Row 1 to Row 2 and mix well (1:100), transferring 15 µL from Row 2 to Row 3 and mix well (1:1000), and Transfer 154, of Row 3 to Row 4 and mix well (1:10,000). If the virus was concentrated, more dilutions may be needed.

To infect cells, remove plating media from HT1080 cells, and infect by transferring 100 µL of the prepared dilutions to each corresponding well (using a multichannel pipette if available). Spin the 96-well infected cell plate at 2000 rpm at room temperature for 30 minutes, and incubate the infected cell plate overnight.

On Day 2 (morning), remove medium containing virus and replace with fresh HT1080 culture medium (without Polybrene®), incubate cells for an additional 3 days, analyze % of GFP positive cells (flow cytometry analysis may be used).

To calculate the titer in units TU/mL, determine appropriate dilution factor to use based on % GFP positivity. A desired infection range of 1-20% may be used.

Titer may be calculated from the following formula:

$$\text{Titer} = [F*C/V]*D$$

F=frequency of GFP+ cells (% GFP+ cells/100)
C=cell number per well at time of transduction (7000 cells)
V=volume of inoculum in mL (0.1 mL)
D=lentivirus dilution factor.

A. A Second Lentiviral Production System Protocol

A second lentiviral production system protocol may be conducted as follows.

Materials:
125 mL, 250 mL, 500 mL and 1 L polycarbonate, disposable, sterile, Vent-up shaker flasks Orbital shaker in temperature 37 C, 8% $CO_2$ and 75-80% humidity controlled Incubator
Equipment and reagents to determine cell viability
Protocol Outline
    Thawing and recovery: 3-4 days
    Subculture: every 3-4 days
    Warm up culture medium to 37° C. before use
    Orbital shaker speed: 125 rpm for 125 mL to 1 L shaker flasks
    Growth properties: High-density suspension growth in special culture medium.
Cell Doubling Time:
    Doubling Time (DT): ~24 hours
    Calculating Formulation: DT=T*LN(2)/LN(Xe/Xb)
    T: Time of cell culture-hours
    Xe: Cell density at the end
    Xb: Cell density at the beginning To ensure viability, monitor cell growth and viability the first 3-4 days to ensure the cells are not compromised. At 24 hours post-thaw, viability may drop to 80%, but should not fall below 70%. By 3-4 days post-thaw, viability should be 90-95%.

Figure 7:
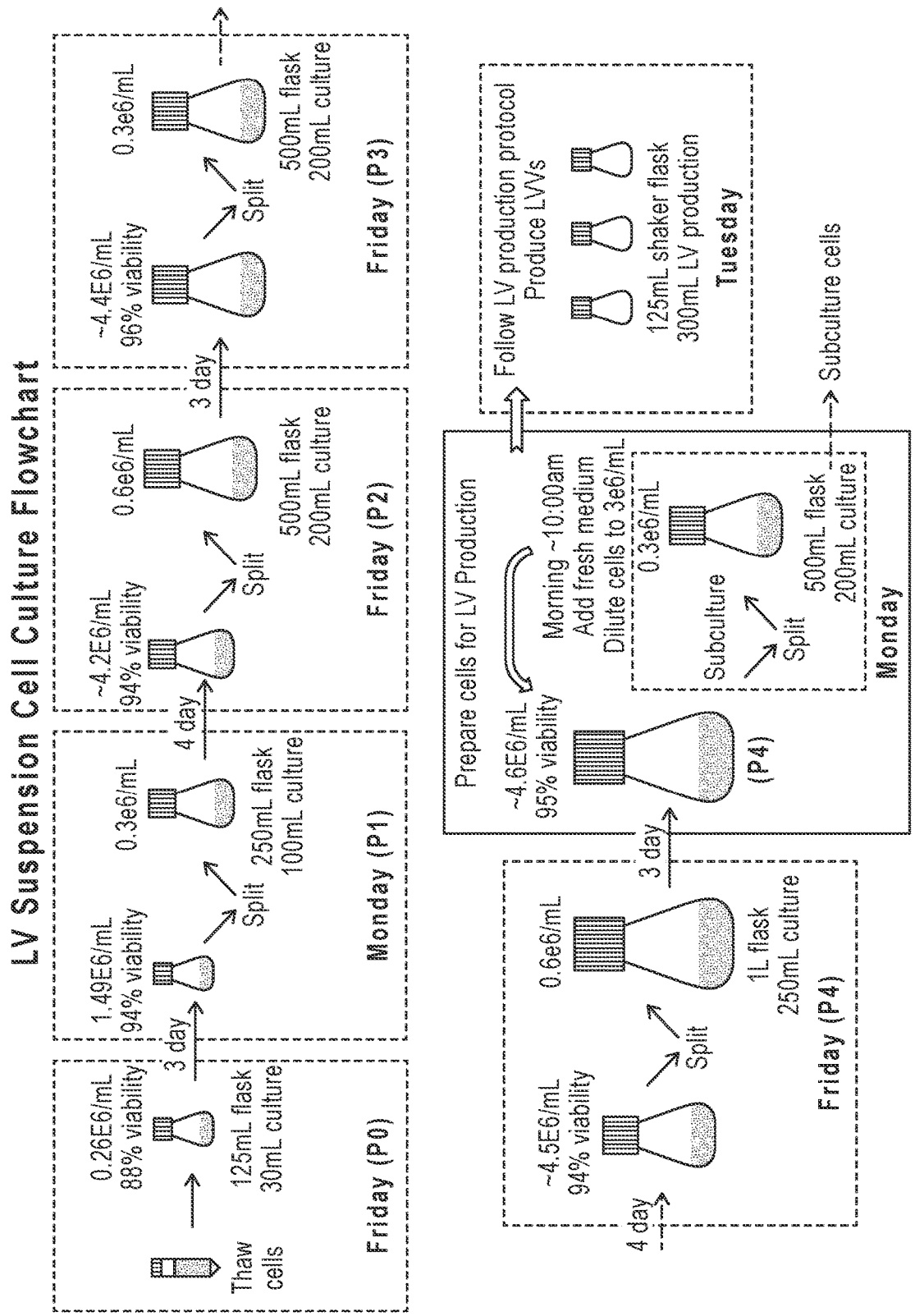
FIG. 7 provides a lentiviral suspension cell culture flowchart corresponding to Example 7.

Subculture conditions. FIG. 7 provides a lentiviral suspension cell culture flowchart that may be followed to culture cells. For subculture, in some embodiments, cells should not be grown above $5 \times 10^6$ cells/mL. Cells may be discarded after passage number 40.

Scaling Up Cell Culture. The cells may be scaled up in shaker, spinner flasks or bioreactors. Determine the optimal shaker, spinner or impeller speed and seeding density for your culture system. In some embodiments, the cells be seeded at $0.3 \times 10^6$ to $0.6 \times 10^6$ viable cells/mL for subculture. Optimum shaker speed is approximately 125 rpm for 125 mL to 1 L shaker flasks, and optimum impeller speed in Celligen® stirred tank bioreactors is 70-100 rpm.

Guidelines to consider. Subculture the cells a minimum of three times to allow them to recover from thawing before using them in transfection experiments. Keep cell densities between $3-5 \times 10^6$ cells/mL of culture for best performance. We recommend maintaining cells in a 250 mL or 500 mL polycarbonate, disposable, sterile Erlenmeyer shaker flask. Working volume of cell suspension is 30-40% of shaker flask size. For example, 500 mL of shaker flask, working volume is 150 mL to 200 mL. Glass flasks may be used, but clean them thoroughly after each use to avoid potential toxicity.

EXAMPLES

Example 1. Cell Culture

LV suspension cells were cultured in polycarbonate, disposable, sterile, Vent-up shaker flasks (125 mL to 1 L) at 30%-40% of shake flask size volume on Orbital shaker at 125 rpm in cell culture incubator (37 C, 8% CO2, 70-80% humidity). Cells were split every 3-4 days, density between $4-5 \times 10^6$/mL.

Example 2. Lentiviral Production Experiment

Based on development needs, lentiviral (LV) production experiments were conducted in two formats: 96-deep well plate and 125 mL shaker flask at 1 mL and 30 mL culture volumes, respectively. Cell density was $4 \times 10^6$/mL. Lentiviral vectors (LVVs) were packed by co-transfection lenti expression (transfer) plasmid—pLenti6.3/V5-GW/EmGFP and lenti packaging plasmid—ViraPower Lentiviral Packaging Mix, total DNA was 3 µg/mL. Opti-MEM® I was the DNA/Reagent complexation medium at 75 uL/mL for both transfection reagent and DNA dilutions; the total complex volume was 150 ul/mL. The complexation time was 10-20 mins. Expifectamine™ 293 was the transfection reagent on LV culture supplement and LV enhancer developments, amounts were various from 5-8 ul/mL. 5% LV culture supplement was included in all the developing experiments. Previous to the developments described herein, 5 mM caffeine was used as an LV enhancer prior and was added at post-transfection 16-18 hrs. Post-transfection 48 hrs., cell supernatant containing LVVs were collected by spinning down the cells and viral titers were measured.

Example 3: Lentiviral Titer Measurement

Lentiviral titers were measured by infecting Ht1080 cells. 4 hours before infection, seed 7000 cells per-well in 96-well plate. At the time infection, cells adhered on the culture vessel at ~30% confluence. Serial dilutions of LVVs from $10^1$ to $10^5$ were performed in culture medium containing 8 ug/mL of Polybrene®. Cells were infected by $10^4$ and $10^5$ viral dilutions. After infection of the cell, the infected Ht1080 plate was spun at room temperature for 30 mins at 2000 rpm. Post -18 hrs infection, medium was changed with fresh culture medium containing no Polybrene®. Cells were incubated for another 72 hrs. and the GFP positive cells measured by Attune Flow Cytometry. The titers were calculated based on percentage GFP cells between 1-20% wells.

At the day of transfection, 30 mL of 3 different cells density cultures were prepare: $2.5 \times 10^6$/mL, $4 \times 10^6$/mL and $5 \times 10^6$/mL in 125 mL shaker flasks. Each density cell had 4 flasks that contained different amounts of LV culture supplement, 0%, 1%, 5% and 10% of 30 mLs, respectively. Each 30 mL of the culture cells was transfected by diluting 210 µl (7 µl/mL) of Expifectamine™ 293 in 2.25 mL of Opti-MEM® I medium and diluting 54 µg ViraPower™ Lentiviral Packaging Mix and 36 µg of pLenti/V5-GW/EmGFP expression vector in 2.25 mL of Opti-MEM® I medium, combining these two solutions—4.5 mL in total and incubating at room temperature for 10 minutes then transfecting the cells. Post-48 hrs transfection, cell culture supernatants were harvested by spinning down the cells.

Results showing the impact of the amount of culture supplementation in lentiviral production are provided in FIG. 1A.

Figure 1B:
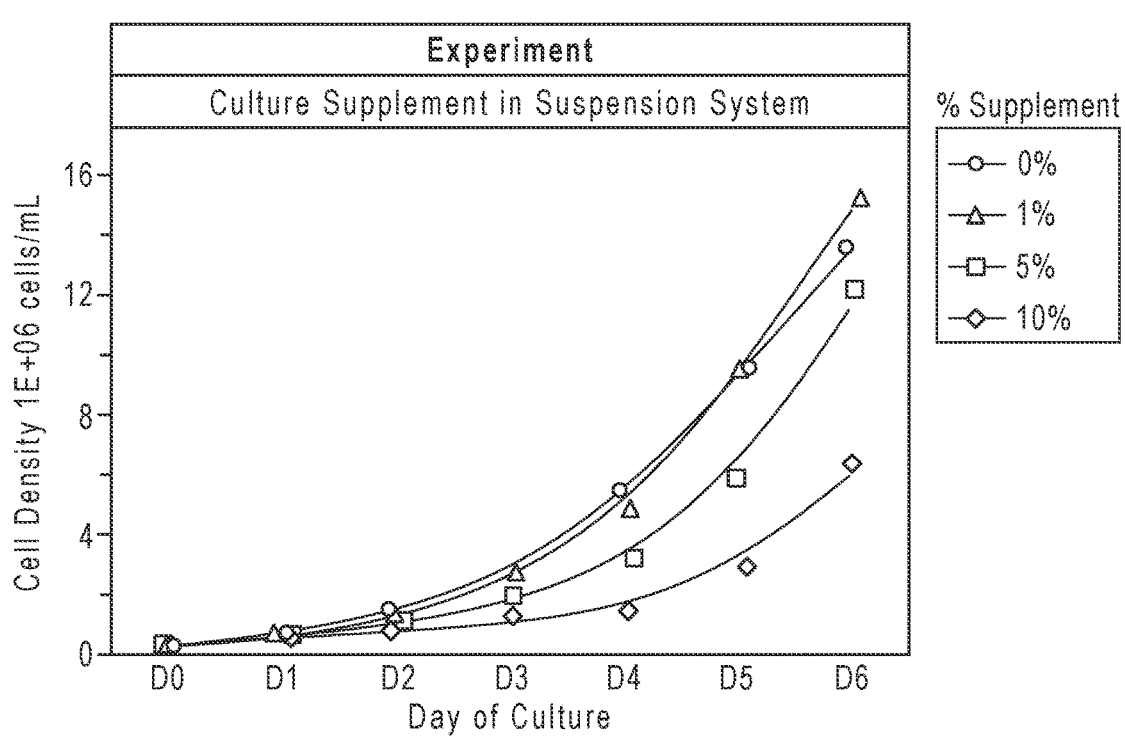

Next, lentiviral suspension cells were cultured under different amounts of LV Culture Supplement from containing 0% to 10% (0%, 1%, 5% and 10%), measured the cell densities each day for 6 days. Results are shown in FIG. 1B.

Example 2: Screening of New Transfection Reagents

Using a JMP® Design of Experiments (DOE) platform, a screening experiment was designed using three core chemicals as potential transfection reagents: DHDMS, DOPE and cholesterol.

The DOE platform allowed investigators to vary multiple parameters simultaneously, instead of varying each of the parameters individually and then considering each optimized parameter for an overall optimized formulation. When second-order effects between parameters can impact results, the DOE platform, varying all candidate parameters simultaneously, allows for a more efficient and accurate result. Experiments using the DOE platform also require fewer runs and are more economical than traditional experimental approaches. See Kauffman et al., Optimization of Lipid Nanoparticle Formulations for mRNA Delivery in Vivo with Fractional Factorial and Definitive Screening Designs, NanoLetters 15:7300-7306 (2015) and supplemental materials for a theoretical discussion on DOE platforms.

DHDMS, DOPE, and cholesterol were evaluated at different mole ratio, with the total of the ingredients valued at 1 at every row in Table 5. In the table, software auto designed repeat runs to control the experimental accuracy, 1×R1 and 1×R2, 1×R6 and 1×R7.

TABLE 5

Lentiviral Transfection Reagent DoE Design

| Run# | DHDMS | DOPE | CHOL |
|---|---|---|---|
| 1×R1 | 0.4000 | 0.0000 | 0.6000 |
| 1×R2 | 0.4000 | 0.0000 | 0.6000 |
| 1×R3 | 0.4000 | 0.2575 | 0.3425 |
| 1×R4 | 0.4000 | 0.2616 | 0.3384 |
| 1×R5 | 0.4000 | 0.5000 | 0.1000 |
| 1×R6 | 0.4965 | 0.2386 | 0.2649 |
| 1×R7 | 0.4965 | 0.2386 | 0.2649 |
| 1×R8 | 0.5000 | 0.5000 | 0.0000 |
| 1×R9 | 0.5200 | 0.0000 | 0.4800 |
| 1×R10 | 0.6000 | 0.0000 | 0.4000 |
| 1×R11 | 0.6000 | 0.2000 | 0.2000 |
| 1×R12 | 0.6000 | 0.4000 | 0.0000 |

Based on Table 5, new transfection reagents were made. These new formulated reagents were used to package GFP LVVs by co-transfection pLenti/V5-GW/EmGFP expression vector and ViraPower™ Lentiviral Package Mix in 96-deep well block, 1 mL of culture volume, 3 μug total DNA (pLenti expression vector+ViraPower™ Packaging Mix, the two vectors at 2:3 (weight:weight) ratio) 5 ul/mL and 6 uL/mL amounts of transfection reagent were studied, cell density at $4\times10^6$/mL, with 5% LV culture supplement. The results shown in FIG. 2A were averages of these two doses, with read out in TU/mL.

Based on this DoE result, we designed more reagents by making different combinations of the test compounds, such as DHDMS with DOPE, DHDMS with cholesterol, and DHDMS with DOPE and cholesterol. We tested each group of new reagents in 30 mL production format and used lipofectamine as a control reagent. We found DHDMS with DOPE had the highest performance amount, specifically at a mole ratio of 0.65 DHDMS to 0.35 DOPE compared to the other two combinations of transfection reagents.

Figure 2A:
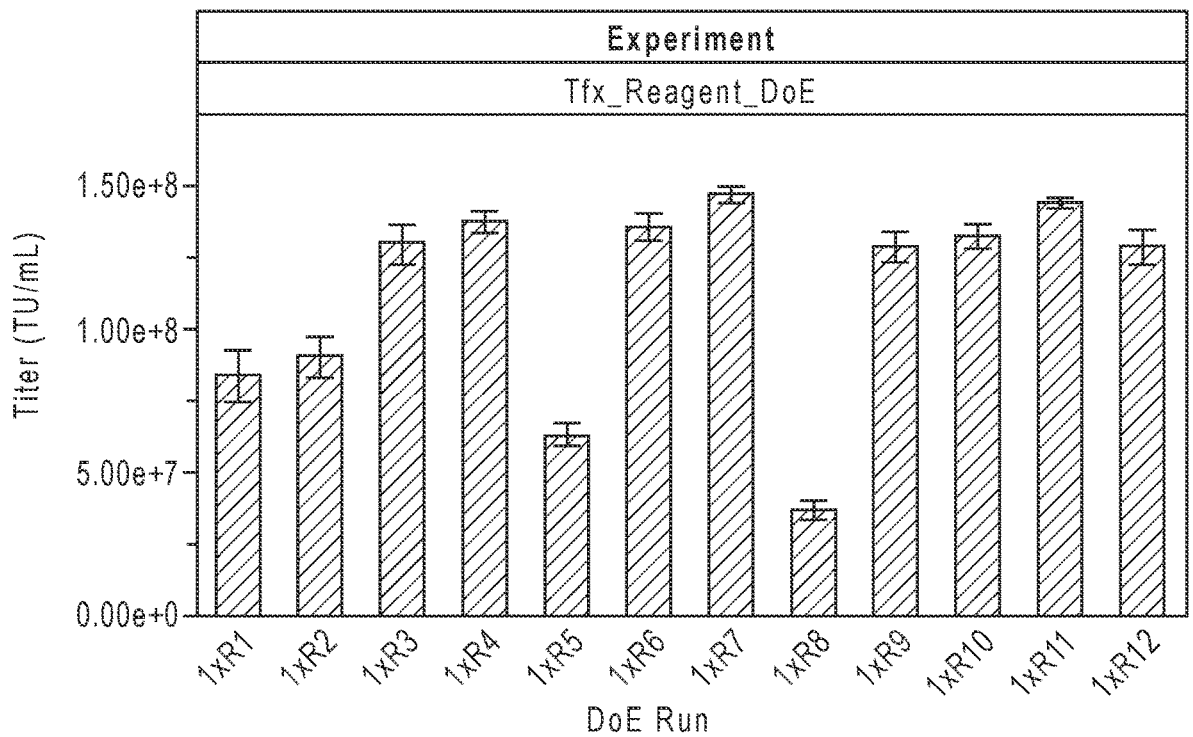
FIGS. 2A-B shows screening of new transfection reagents.
Figure 2B:
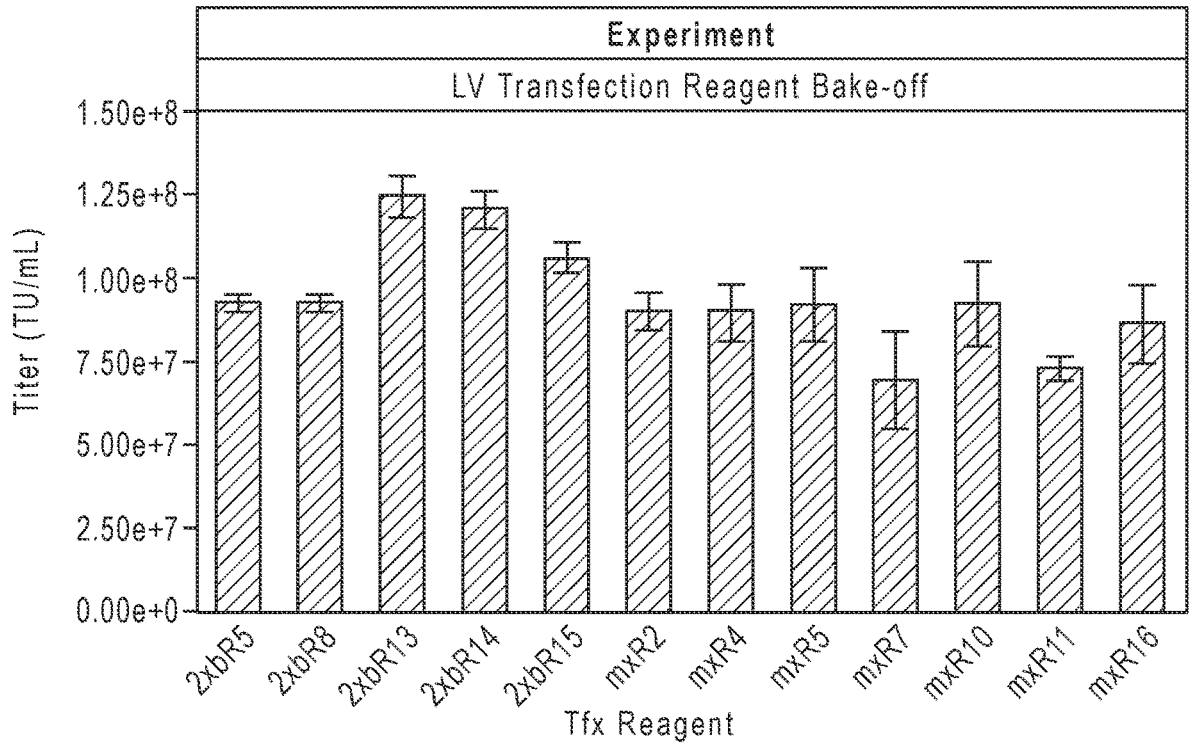

Twelve reagents were chosen based on performance and formulation compositions and the lentiviral transfection reagents in this bake-off run are shown in Table 6. Results are shown in FIG. 2B.

TABLE 6

Lentiviral Transfection Regents Bake-Off Formulation

| Run# | DHDMS | DOPE | CHOL |
|---|---|---|---|
| 2bxR5 | 0.406 | 0.131 | 0.463 |
| 2bxR8 | 0.413 | 0.077 | 0.510 |
| 2bxR13 | 0.473 | 0.228 | 0.299 |
| 2bxR14 | 0.512 | 0.208 | 0.279 |
| 2bxR15 | 0.519 | 0.126 | 0.355 |
| mxR2 | 0.483 | 0.231 | 0.285 |
| mxR4 | 0.497 | 0.239 | 0.265 |
| mxR5 | 0.519 | 0.279 | 0.201 |
| mxR7 | 0.550 | 0.450 | 0.000 |
| mxR10 | 0.577 | 0.294 | 0.129 |
| mxR11 | 0.600 | 0.000 | 0.400 |
| mxR16 | 0.650 | 0.350 | 0.000 |

Example 3: Identification of Lentiviral Enhancers

Lentiviral enhancers were identified using the following experiment. Two 96-deep blocks were transfected by Expifectamine™ 293 transfection reagent complexed with pLenti6.3/V5-GW/EmGFP and ViraPower Lentivirus Packaging Mix. For each well (1 mL reaction), two solutions were combined: 7 μl of Expifectamine™ 293 in 75 μl of Opti-MEM® I medium and 3 μg total DNA (1.2 μg pLenti expression vector and 1.8 μg ViraPower™ mix) in 75 μl of Opti-MEM® I, for a total 150 μL complex. Cells were transfected at $4\times10^6$/mL, with 5% LV Culture Supplement. Post-16 hrs transfection, prepared lentiviral enhancers designed by JMP® were added, according to Table 7, triplicated for each lentiviral enhancer.

TABLE 7

Lentiviral Enhancer DoE

| Run# | Valproic Acid | Sodium Propionate | Sodium Butyrate | Caffeine |
|---|---|---|---|---|
| 1×R1 | 0 | 7.5 | 0 | 0 |
| 1×R2 | 0 | 7.5 | 0 | 1.5 |
| 1×R3 | 0 | 7.5 | 0 | 1.5 |
| 1×R4 | 0 | 7.5 | 3 | 0 |
| 1×R5 | 0 | 7.5 | 3 | 0.75 |
| 1×R6 | 0 | 7.5 | 3 | 1.5 |
| 1×R7 | 0 | 11.25 | 3 | 0 |
| 1×R8 | 0 | 15 | 0 | 0 |
| 1×R9 | 0 | 15 | 0 | 0 |
| 1×R10 | 0 | 15 | 0 | 1.5 |
| 1×R11 | 0 | 15 | 1.5 | 1.5 |
| 1×R12 | 0 | 15 | 3 | 0. |
| 1×R13 | 0 | 15 | 3 | 1.5 |
| 1×R14 | 0.5 | 7.5 | 1.5 | 0 |
| 1×R15 | 0.5 | 11.25 | 1.5 | 0.75 |
| 1×R16 | 0.5 | 11.25 | 1.5 | 0.75 |
| 1×R17 | 0.5 | 11.25 | 3 | 1.5 |
| 1×R18 | 0.5 | 15 | 0 | 1.5 |
| 1×R19 | 0.5 | 15 | 3 | 0.75 |
| 1×R20 | 1 | 7.5 | 0 | 0 |
| 1×R21 | 1 | 7.5 | 0 | 1.5 |
| 1×R22 | 1 | 7.5 | 3 | 0 |
| 1×R23 | 1 | 7.5 | 3 | 0.75 |
| 1×R24 | 1 | 7.5 | 3 | 1.5 |
| 1×R25 | 1 | 11.25 | 0 | 0.75 |
| 1×R26 | 1 | 11.25 | 3 | 0 |
| 1×R27 | 1 | 15 | 0 | 0 |
| 1×R28 | 1 | 15 | 0 | 1.5 |
| 1×R29 | 1 | 15 | 1.515 | 1.5 |
| 1×R30 | 1 | 15 | 3 | 0 |
| 1×R31 | 1 | 15 | 3 | 1.5 |
| R_ctrl | 0 | 0 | 0 | 5 |

Figure 3A:
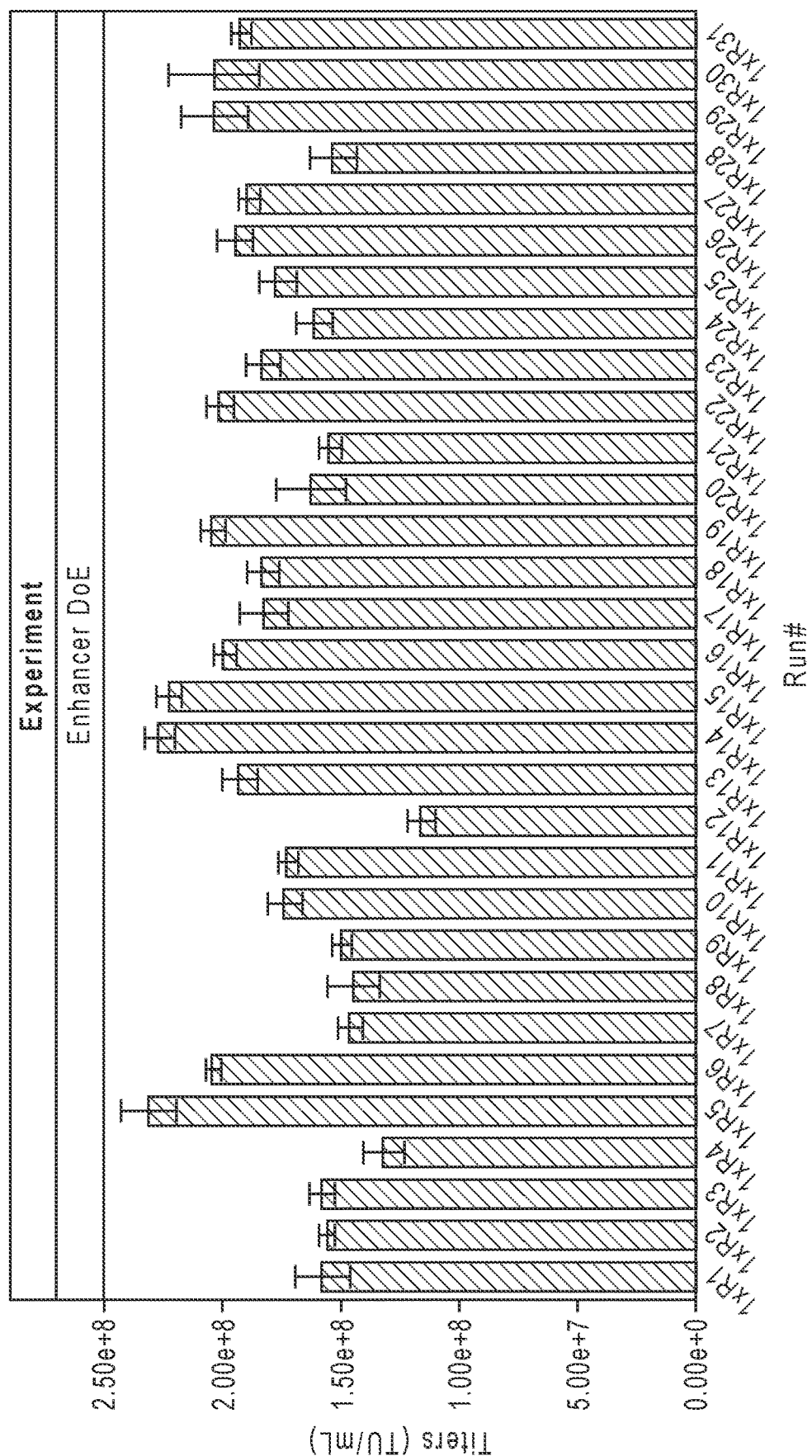
FIGS. 3A-3C show identification of lentiviral enhancers. The bake-off experiment for identifying new lentiviral enhancer leads was designed by using JMP® software for DoE.

Post-48 hrs transfection, lentivirus titration assay was conducted. Results are shown in FIG. 3A.

Figure 3B:
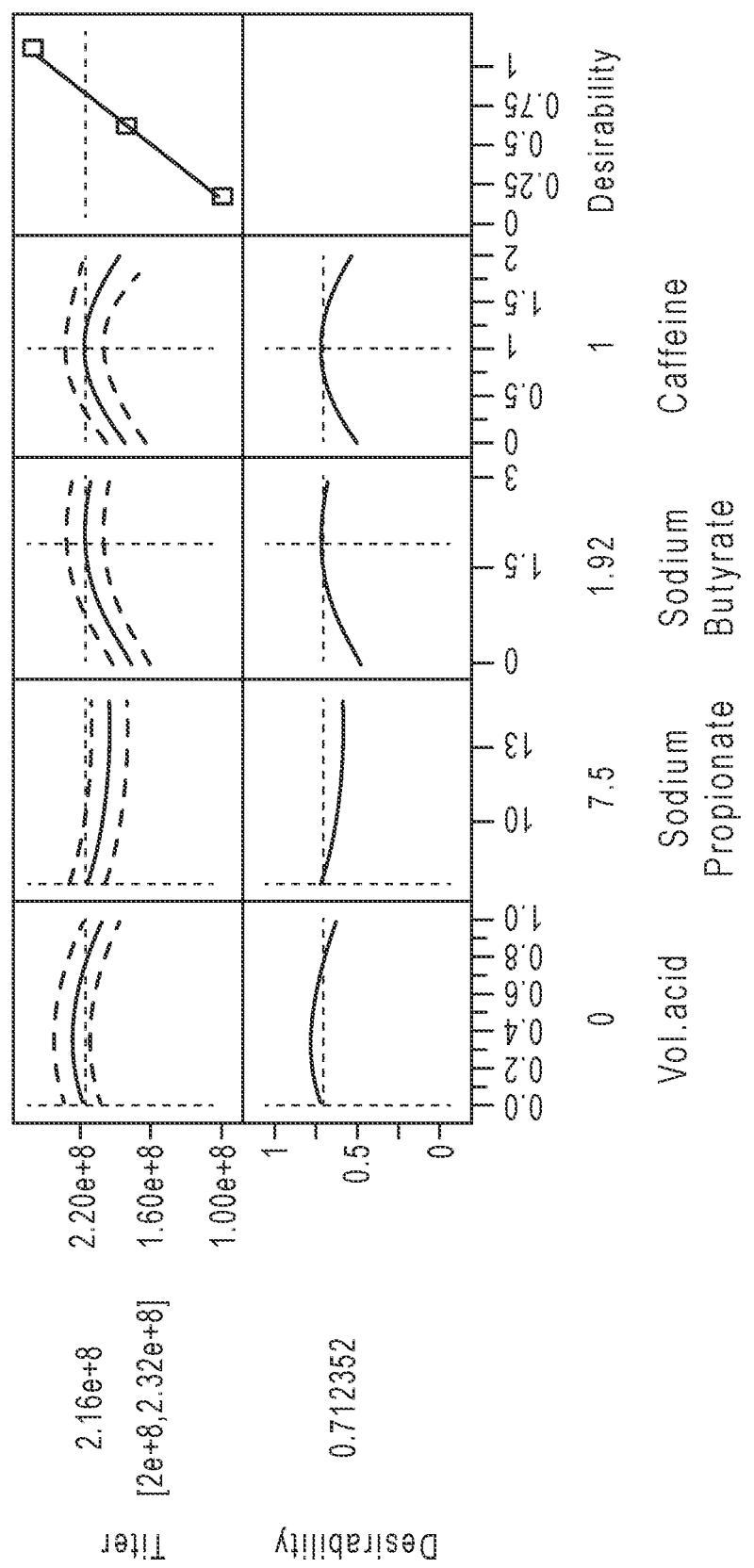

Results were analyzed by jmp, prediction profiler was graphed in FIG. 3B. Secondary DoE was designed and analyzed as below, with an optimized condition found (see Table 8).

TABLE 8

Enhancer Secondary DoE

| Run# | Sodium Propionate | Sodium Butyrate | Caffeine |
|---|---|---|---|
| 2xR1 | 3.00 | 1.00 | 0.50 |
| 2xR2 | 3.00 | 1.00 | 1.50 |
| 2xR3 | 3.00 | 1.50 | 0.50 |
| 2xR4 | 3.00 | 2.00 | 0.50 |
| 2xR5 | 3.00 | 2.00 | 1.00 |
| 2xR6 | 3.00 | 2.00 | 1.50 |
| 2xR7 | 6.50 | 1.50 | 1.00 |
| 2xR8 | 6.50 | 1.50 | 1.00 |
| 2xR9 | 6.50 | 2.00 | 0.50 |
| 2xR10 | 10.00 | 1.00 | 0.50 |
| 2xR11 | 10.00 | 1.00 | 1.50 |
| 2xR12 | 10.00 | 1.50 | 0.50 |
| 2xR13 | 10.00 | 2.00 | 0.50 |
| 2xR14 | 10.00 | 2.00 | 1.00 |
| 2xR15 | 10.00 | 2.00 | 1.50 |

Figure 3C:
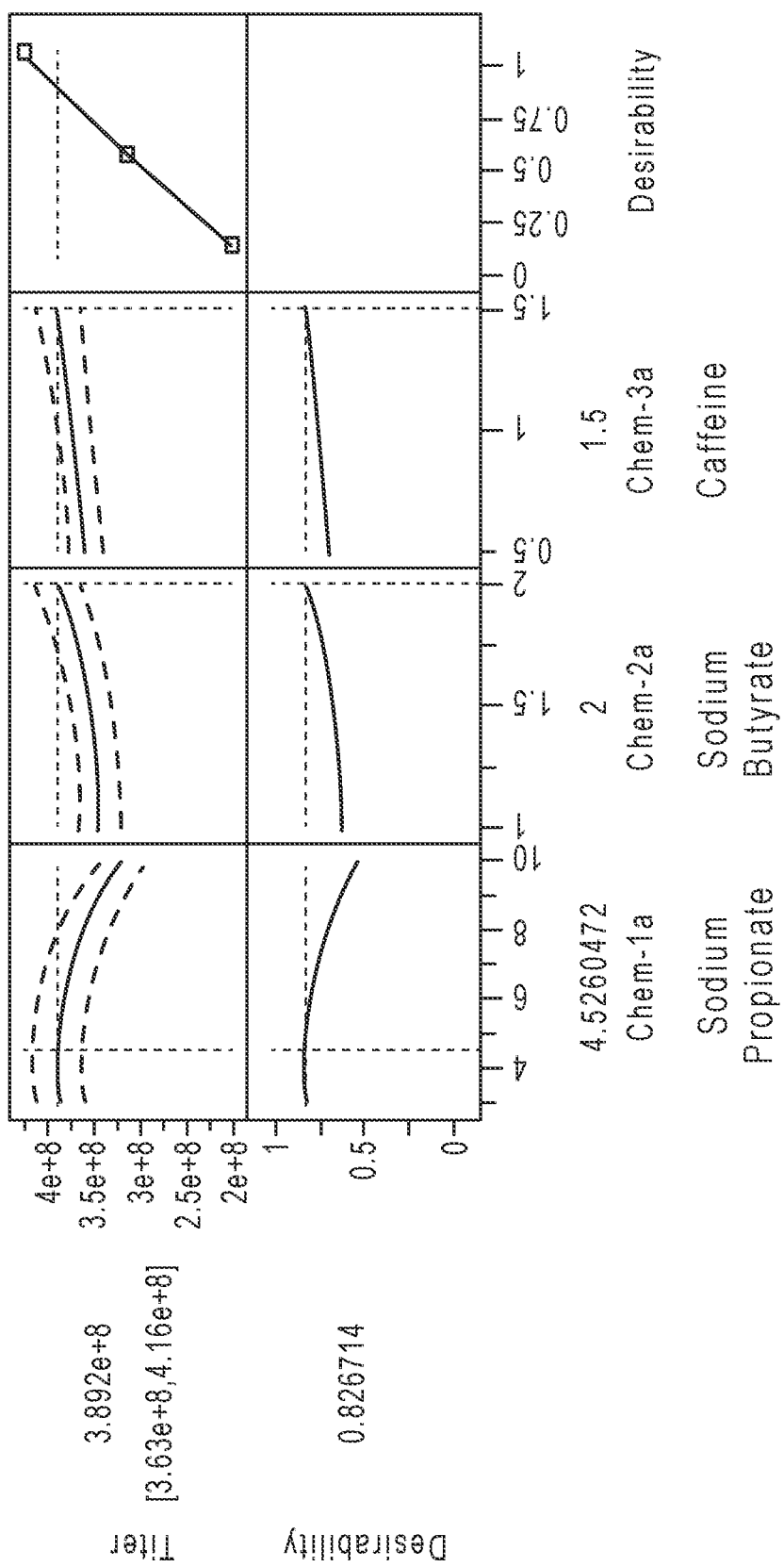

Results were analyzed by jmp, and the prediction profiler was graphed in FIG. 3C.

Example 4: Lentiviral Production System Comparison

We compared our new developed suspension lentiviral production system using Lentifectamine™, Thermo Fisher, (LVR) as a transfection reagent with PEI-mediated (a 25 KD linear polymer), and Lipofectamine™ 2000-mediated (LK2) transfection techniques for lentiviral production, varying the transfection reagents and varying whether the production process contained or did not contain lentiviral culture supplement, lentiviral enhancer, and/or sodium butyrate.

Transfection in the LV293 system was performed as follows. The system was a 125 mL shaker flask with 30 mL LV production. LV293 cells, derived from 293F cells, were seeded with a density at 3.5M/mL at the time of transfection. When used, the final concentration for the lentiviral culture supplement was 3.5%, enhancer was 4%, sodium butyrate was 5 mM. Culture supplement was ExpiCHO™-Feed and lentiviral enhancer was 4.53 mM sodium propionate, 2.0 mM sodium butyrate, and 1.5 mM caffeine.

Briefly, cells were counted at the day of transfection and diluted in a final 25.5 mL system, with culture supplement whenever the sample called for it. TubeA: Transfection reagents (either LVR or L2K (Lipofectamine 2000) were mixed in 2.25 mL Gibco™ Opti-MEM™, incubated for 5 min at room temperature. TubeB: DNA mixture (ViraPower™ Lentiviral mixture 45 ug and 30 ug pLenti6.3/V5-GW/GFP) was diluted in another 2.25 mL Gibco™ Opti-MEM™. TubeB then was added to TubeA, mixed and incubated for 10 min at room temperature. The final mixture (approximately 4.5 mL) was added to the prepared cells. 16 hrs post-transfection 1.2 mL (4% of production volume) enhancer was added when called for in the sample. Sodium butyrate was added 24 hrs post-transfection when called for in the sample. Supernatants were harvest 48 hrs post transfection and titer was performed as described.

For transfection in 293F cells, the final cell density was 1M/mL. Total DNA amount was reduced to 1 ug/mL (ViraPower™ Lentiviral mixture 18 ug and 12 ug pLenti6.3/V5-GW/GFP for 30 mL system). Unless stated, the transfection and virus harvest procedures were the same as those in LV293 system.

Figure 4:
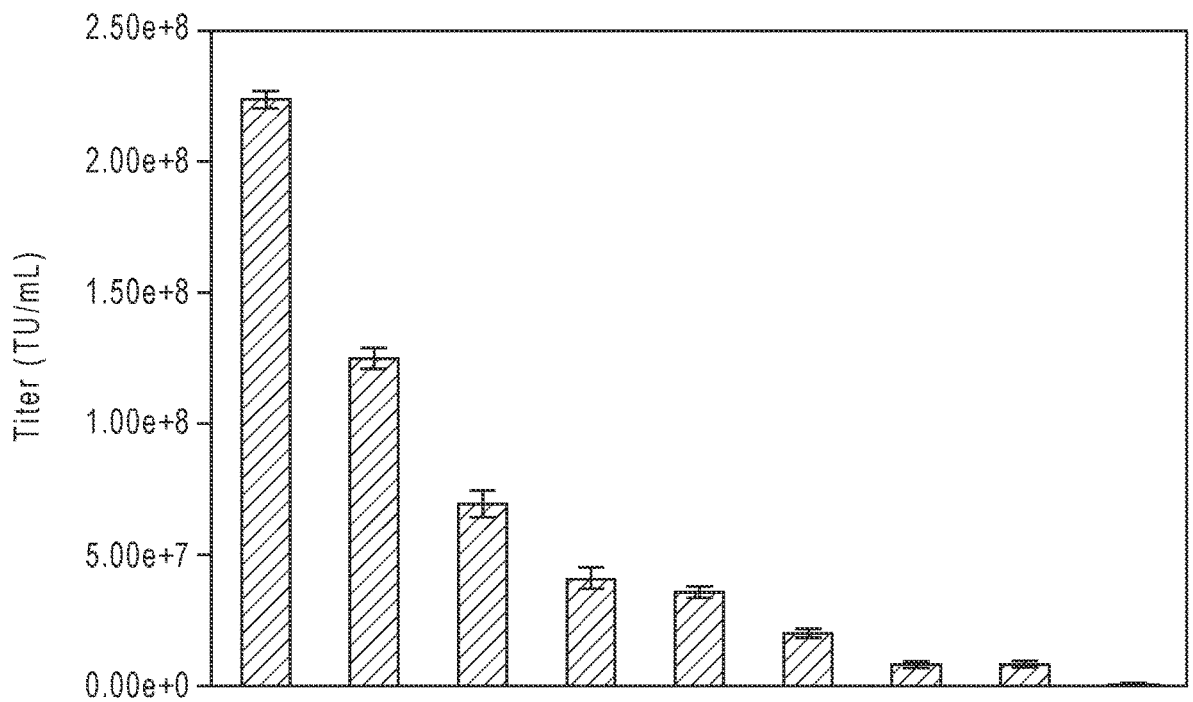
FIG. 4 provides results from a lentiviral production system comparison. Specifically, it shows titer per ml of lentiviral vector using different transfection reagents, presence or absence of lentiviral culture supplement, presence or absence of lentiviral enhancer, and presence or absence of sodium butyrate.

Our lentiviral production is superior than the other two systems, as shown in FIG. 4A.

Example 5: A First Lentiviral Production Protocol

The following guidelines for culture of lentiviral suspension cells were followed. The cells were grown according to standard lentiviral suspension cell culture protocols. The cells were subcultured when they reached a density of approximately $4 \times 10^6$ to $5 \times 10^6$ viable cells/mL, typically every 3-4 days. The cells were be split to $0.3 \times 10^6$ to $0.6 \times 10^6$ cells, after about 3 or 4 days of culture. The cell growth were monitored by counting the cells daily at the same time every day. Cell doubling time was about 24 hours. After two weeks from the thawing date, cells were ready for lentiviral production. During cell culture, an orbital shaker was used at about 125 rpm for 125 mL to 1 L shaker flasks. The incubator was set to about 37° C., about 8% $CO_2$, and about 75-80% humidity. The culture medium was warmed in an about 37° C. water bath before use.

Reagents and Methods:
- 125 mL polycarbonate, disposable, sterile, Vent-up Erlenmeyer shaker flask;
- 15 mL sterile conical tube;
- 50 mL sterile conical tube;
- Opti-MEM™ I medium;
- Lenti expression (transfer) vector: pLENTI6.3/V5-GW-EmGFP;
- Lenti packaging mix: ViraPower™ Lentiviral Packaging Mix;
- Lentiviral suspension cells;
- Lentiviral culture supplement;
- Lentiviral transfection reagent;
- Lenitviral enhancer
- (Optional) Lentiviral stabilizer for adjusting pH If cells are split on Friday morning to a cell count of $0.6 \times 10^6$ cells/mL, for example, they may be cultured for 3 days in 1 L flask at about 250 mL culture medium. On Monday morning at 10:00 am, for example, the cells are prepared by counting the cells, and a cell density of around $4.5 \times 10^6$ cells/mL may be expected. The cells may be diluted in fresh warmed culture medium to $3.0 \times 10^6$ cells/mL and cultured for another 30 hours.

The transfection may be carried out on Tuesday afternoon at 4:00 pm, for example. The cells may be counted with about 5.5 to $6.0 \times 10^6$ cells/mL expected. Table 9 provides additional transfection guidelines.

TABLE 9

Transfection of Cells

| | 1 mL | 30 mL |
|---|---|---|
| Cell Density ($1 \times 10^6$ cells/mL) | $3.5 \times 10^6$ cells/mL | $105 \times 10^6$ cells/mL |
| % LV Culture Supplement | 3.5% (350 µl) | 3.5% (1.05 mL) |
| Total DNA (µg) | 2.5 µg (1.5 µg + 1 µg) | 75 µg (45 µg + 30 µg) |
| ViraPower™: pLenti = 3:2 (µg:µg) | | |
| LV Transfection Reagent | 5 µL | 150 µL |
| Opti-MEM™ I (for complexation) | 2 × 75 µL | 2 × 2.25 mL |
| LV Enhancer | 40 L | 1.2 mL |
| LV Stabilizer | 10 µL | 300 µL |

On Tuesday afternoon, the cells were seeded with lentiviral supplement. If a 30 mL transfection was selected it may be conducted with high density cells, such as $105 \times 10^6$ cells/mL in 17.5 mL. 3.5% lentiviral culture supplement was added, which would be 1.5 mL in a 30 mL transfection. Fresh warmed culture medium was used to a total volume of 25.5 mL (6.95 mL of fresh media because 1.05 mL of lentiviral culture supplement and 17.5 mL of cell suspension were used). The other 4.5 mL to achieve a total volume of 30 mL was added from the DNA/reagent complex.

The DNA/transfection reagent was prepared as follows. Two tubes were labeled Tube-1 and Tube-2. In Tube-1: 2.25 of Opti-MEM™ I medium and 150 µL of lentiviral transfection reagent was mixed and incubated for about 5 minutes at room temperature. In Tube-2: 2.25 mL of Opti-MEM™ I medium was mixed with 45 µg (µL) ViraPower™ Lentiviral Packaging Mix (ViraPower™ 1 µg/µL) and 30 µg (µL) pLenti6.3/V5-GW/EmGFP plasmid (pLenti expression vector 1 µg/µL). Tube-1 and Tube-2 was combined by adding Tube-2 solution to Tube-1 with mixing.

The complex solution was incubated at room temperature for 10 minutes. After 10 minutes of incubation, 4.5 mL of DNA/reagent complex was added to the prepared cells.

The next day (Wednesday morning, at 9:00 am), 1.2 mL of LV Enhancer was added to the flask.

At 48 hours post transfection (Thursday afternoon, at 4:00 pm), harvested LVVs in a 50 mL sterile conical tube and spun down the cells at 3000 rpm, at room temperature for 10 minutes. Collected the supernatant and spun again at 3000 rmp for 10 minutes. Collected the supernatant and ran through a 0.45 µM filter.

Added lentiviral stabilizer to the collected supernatant in order to adjust the pH after the virus has been harvested. Lentiviral stabilizer was added as 1% of the collected supernatant (300 µL). In some situations, the production system pH was adjusted from about 5 to 8 to stabilize the virus.

Stored the lentiviral vectors in 4 C for the next day purification and measured the virus titer by infecting Ht1080 cells at serial dilutions of lentiviral vectors, as described in Example 6.

Example 6: Measurement of Lentiviral Titer (GFP+) from the Production in Example 5

Measurement of lentiviral titer (GFP+) was conducted as follows.
Materials:
Lentivirus: collect cell supernatant or concentrated lentiviral vectors;
Cell line: HT1080;
Culture Medium: Gibco™ DMEM high glucose, GlutaMAX™ Supplement, pyruvate+10% FBS;
Polybrene™ (stock solution): 100 mg/mL in sterile $H_2O$ (Fisher Scientific NC0663391); and
Costar® 96-well round bottom plate for dilutions (Fisher Scientific 05539200).

On Day 1 (morning), we began the measurement of lentiviral titer using a 96-well plate format for high throughput flow analysis. In the morning at 11:00 am, we seeded a 96-well plate with HT1080 cells at a density of 7000 cells/well in 100 µL of culture media (~30% confluent at time of infection).

In the afternoon at 4:00 pm, we prepared fresh virus dilutions as follows. (A) We combined 15 mL of fresh culture medium and 12 µL of 10 mg/mL Polybrene® (final concentration of 8 µg/mL). Vortexed well to combine. (B) Per-viral sample, added 135 µL of medium prepared in (A) to 16 wells of a 96-well round bottom plate in a 4-well-by-4-well pattern (see FIG. 6). (C) Added 15 µL of one sample of lentiviral supernatant (or concentrated viral aliquot) to each well in row 1 (total volume 150 µL in each well). (D) Mixed well using a pipette (1:10). (E) Performed serial dilution of Row 1 (using a multichannel pipette if available) by transferring 15 µL from Row 1 to Row 2 and mix well (1:100), transferring 15 µL from Row 2 to Row 3 and mix well (1:1000), and Transfer 15 µL of Row 3 to Row 4 and mix well (1:10,000). If the virus is concentrated, more dilutions may be needed.

To infect cells, removed plating media from HT1080 cells, and infected by transferring 100 µL of the prepared dilutions to each corresponding well (using a multichannel pipette if available). Spun the 96-well infected cell plate at 2000 rpm at room temperature for 30 minutes, and incubated the infected cell plate overnight.

On Day 2 (morning), removed medium containing virus and replaced with fresh HT1080 culture medium (without Polybrene®), incubated cells for an additional 3 days, analyzed % of GFP positive cells (flow cytometry analysis may be used).

To calculate the titer in units TU/mL, we determined appropriate dilution factor to use based on % GFP positivity. A desired infection range of 1-20% was used.

Titer was calculated from the following formula:

$$\text{Titer} = [F*C/V]*D$$

F=frequency of GFP+ cells (% GFP+ cells/100)
C=cell number per well at time of transduction (7000 cells)
V=volume of inoculum in mL (0.1 mL)
D=lentivirus dilution factor.

Using a 96-well protocol, the following calculations were performed (see Table 10):

TABLE 10

| Lentiviral Titer Calculation | |
|---|---|
| Lentivirus Dilution | % EmGFP Positive Cells |
| $10^2$ | 96% |
| $10^3$ | 65% |
| $10^4$ | 18% |

$10^4$ was chosen for the calculation because the % EmGFP positive cell value falls within the desired 1-20% range.
F=18/100
C=7000
V=0.1
D=$10^4$
Titer=$(0.18*7000/0.1)*10^4 = 1.26 \times 10^8$ TU/mL

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded to the nearest significant figure.

What is claimed is:

1. A method for lentiviral vector production comprising:
   a) culturing a suspension of 293 cells in a serum-free medium;
   b) providing a lentiviral culture supplement to control cell growth, wherein the lentiviral culture supplement comprises amino acids and sugar sources and has an osmolality of about 1000 mOsm/kg to about 1500 mOsm/kg, and wherein the lentiviral culture supplement is provided to the suspension at from about 1% to about 10%, volume/volume;
   c) transfecting the 293 cells with a lentiviral vector using a transfection reagent comprising a cationic lipid and at least one helper and/or neutral lipid; and
   d) providing a lentiviral production enhancer comprising sodium propionate, sodium butyrate, and caffeine capable of boosting lentiviral production.

2. The method of claim 1, wherein the suspension has a cell density of at least $1 \times 10^6$ cells/mL.

3. The method of claim 1, wherein the suspension has a cell density of at least $10 \times 10^6$ cells/mL.

4. The method of claim 1, wherein the suspension has a cell density of at least $20 \times 10^6$ cells/mL.

5. The method of claim 1, wherein the 293 cells are 293F cells or a derivative of 293F cells.

6. The method of claim 1, wherein the lentiviral culture supplement comprises amino acids and/or dipeptides and sugar sources, sugar alcohol, and/or carbon sources.

7. The method of claim 1, wherein the volume of the suspension is from about 10 mL to about 5 L.

8. The method of claim 1, wherein the cell viability is at least 80% after 5 days.

9. The method of claim 1, wherein the cationic lipid comprises dihydroxyl-dimyristylspermine tetrahydrochloride (DHDMS).

10. The method of claim 1, wherein the at least one helper and/or neutral lipid comprises dioleoylphosphatidylethanolamine (DOPE).

11. The method of claim 1, wherein the at least one helper and/or neutral lipid comprises cholesterol.

12. The method of claim 1, wherein the at least one helper and/or neutral lipid comprises DOPE and cholesterol.

13. The method of claim 6, wherein the lentiviral culture supplement has an osmolality of about 1100 mOsm/kg to about 1400 mOsm/kg, about 1200 mOsm/kg to about 1300 mOsm/kg, or any osmolality or range therebetween.

14. The method of claim 6, wherein each of the amino acids has a concentration of about 0.1 mg/ml to about 8 mg/ml.

* * * * *